United States Patent
Crews et al.

(10) Patent No.: US 11,357,483 B2
(45) Date of Patent: Jun. 14, 2022

(54) SURGICAL INSTRUMENT WITH FLEXIBLE SHAFT AND ACTUATION ELEMENT GUIDE

(71) Applicant: Intuitive Surgical Operations, Inc., Sunnyvale, CA (US)

(72) Inventors: Samuel T. Crews, Palomar Park, CA (US); Nicole Kernbaum, Sunnyvale, CA (US); Lawrence Kerver, Campbell, CA (US); Harsukhdeep Singh Ratia, Foster City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1131 days.

(21) Appl. No.: 14/864,272

(22) Filed: Sep. 24, 2015

(65) Prior Publication Data

US 2016/0089213 A1    Mar. 31, 2016

Related U.S. Application Data

(60) Provisional application No. 62/056,232, filed on Sep. 26, 2014.

(51) Int. Cl.
*A61B 17/00* (2006.01)
*A61B 34/30* (2016.01)
*A61B 90/70* (2016.01)

(52) U.S. Cl.
CPC ........ *A61B 17/00234* (2013.01); *A61B 34/30* (2016.02); *A61B 90/70* (2016.02);
(Continued)

(58) Field of Classification Search
CPC ... A61B 17/00234; A61B 34/30; A61B 90/70; A61B 2090/701; A61B 2017/00314; A61B 2017/00327
See application file for complete search history.

(56) References Cited

U.S. PATENT DOCUMENTS 4,688,555 A * 8/1987 Wardle ................. A61B 1/0052
600/149
5,271,543 A * 12/1993 Grant ................... A61B 17/115
227/179.1

(Continued)

FOREIGN PATENT DOCUMENTS

| WO | WO-2015023888 A1 | 2/2015 |
| WO | WO-2015127231 A1 | 8/2015 |
| WO | WO-2015127250 A1 | 8/2015 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Jing Rui Ou
(74) *Attorney, Agent, or Firm* — Jones Robb, PLLC

(57) ABSTRACT

A surgical instrument includes a shaft, a force transmission mechanism disposed at a first end of the shaft, an end effector disposed at a second end of the shaft, an actuation element that extends along the shaft from the force transmission mechanism to the end effector, and an actuation element guide extending along the shaft. The actuation element guide defines a lumen in which the actuation element guide is received. The actuation element guide is compressed into a pre-compressed state along at least a portion of an axial length of the shaft. The actuation element guide can be compressed between first and second blocks of the instrument. The instrument can include a flush tube configured to receive a cleaning fluid, with the actuation element guide being in flow communication with the flush tube to receive the cleaning fluid in the lumen of the actuation element guide.

18 Claims, 18 Drawing Sheets

(52) U.S. Cl.
CPC .............. *A61B 2017/00314* (2013.01); *A61B 2017/00327* (2013.01); *A61B 2090/701* (2016.02)

(56) References Cited

U.S. PATENT DOCUMENTS

| | | | | |
|---|---|---|---|---|
| 5,405,344 A * | 4/1995 | Williamson | ....... | A61B 17/1285 606/1 |
| 5,752,973 A * | 5/1998 | Kieturakis | ............. | A61B 17/29 606/205 |
| 6,817,974 B2 | 11/2004 | Cooper et al. | | |
| 7,320,700 B2 | 1/2008 | Cooper et al. | | |
| 7,410,483 B2 * | 8/2008 | Danitz | ................. | A61B 1/0053 606/1 |
| 7,699,835 B2 * | 4/2010 | Lee | ...................... | A61B 17/062 606/1 |
| 8,545,515 B2 | 10/2013 | Prisco et al. | | |
| 2001/0031983 A1 * | 10/2001 | Brock | .................... | A61B 34/71 606/205 |
| 2001/0047124 A1 * | 11/2001 | Yamamoto | ............. | A61B 10/06 600/101 |
| 2002/0029006 A1 * | 3/2002 | Turturro | ............. | A61B 10/0266 600/562 |
| 2002/0068868 A1 * | 6/2002 | Thompson | ........ | A61M 25/0136 600/434 |
| 2002/0099261 A1 * | 7/2002 | Lien | ....................... | A61H 19/44 600/38 |
| 2003/0045900 A1 * | 3/2003 | Hahnen | ............ | A61B 17/07207 606/205 |
| 2004/0138525 A1 * | 7/2004 | Saadat | ................. | A61B 1/0055 600/104 |
| 2004/0138700 A1 * | 7/2004 | Cooper | .................. | A61B 1/008 606/205 |
| 2005/0240218 A1 * | 10/2005 | Freed | ..................... | A61B 10/04 606/205 |
| 2005/0273084 A1 * | 12/2005 | Hinman | ................. | A61B 1/008 606/1 |
| 2006/0020287 A1 * | 1/2006 | Lee | ...................... | A61B 17/062 606/205 |
| 2009/0088792 A1 * | 4/2009 | Hoell, Jr. | ............... | A61B 17/29 606/206 |
| 2010/0160724 A1 * | 6/2010 | Prisco | .................... | A61B 17/29 600/101 |
| 2011/0071347 A1 * | 3/2011 | Rogers | ............... | A61B 1/00149 600/104 |
| 2011/0071543 A1 * | 3/2011 | Prisco | ............ | A61B 17/0218 606/130 |
| 2011/0152609 A1 * | 6/2011 | Trusty | .................... | A61B 90/50 600/102 |
| 2012/0165829 A1 * | 6/2012 | Chen | ..................... | A61B 17/29 606/130 |
| 2012/0215220 A1 | 8/2012 | Manzo et al. | | |
| 2012/0277762 A1 | 11/2012 | Lathrop et al. | | |
| 2013/0072948 A1 * | 3/2013 | States, III | .......... | A61B 17/0483 606/145 |
| 2013/0325031 A1 | 12/2013 | Schena et al. | | |
| 2013/0325033 A1 | 12/2013 | Schena et al. | | |

* cited by examiner

SURGICAL INSTRUMENT WITH FLEXIBLE SHAFT AND ACTUATION ELEMENT GUIDE

RELATED APPLICATIONS

This patent application claims priority to and the benefit of the filing date of U.S. Provisional Patent Application 62/056,232, entitled "SURGICAL INSTRUMENT WITH FLEXIBLE SHAFT AND ACTUATION ELEMENT GUIDE," filed Sep. 26, 2014, which is incorporated by reference herein in its entirety

TECHNICAL FIELD

The present disclosure relates to surgical instruments that include flexible shafts and actuation element guides, and to related systems and methods.

BACKGROUND

Remotely controlled surgical instruments, including manually operated (e.g., laparscopic) and teleoperated (e.g., robotically controlled) surgical instruments are often used in minimally invasive medical procedures. During medical procedures, surgical instruments may be moved in one or more degrees of freedom. For instance, the surgical instrument may be actuated by transmitting forces from a force transmission mechanism at a proximal end of the surgical instrument shaft to orient and position an end effector located at a distal end of the surgical instrument in a desired location. The surgical instrument may further include a wrist, such as a jointed, articulatable structure, that the end effector is connected to so that the end effector may be positioned relative to the shaft. The surgical instrument may further include one or more actuation elements that extend from the force transmission mechanism and pass through the surgical instrument to actuate the end effector and/or a wrist.

Surgical instruments may be used with cannulas comprising a curved section. To insert a surgical instrument through the curved section to a surgical site within a patient, the shaft of the surgical instrument can be flexible but also provide a degree of stiffness to support the surgical instrument, and in particular the end effector, to perform a surgical procedure. It may be desirable to provide surgical instrument configurations that address challenges associated with advancing a surgical instrument through a cannula having a curved section during a minimally invasive surgical procedure.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical instrument comprises a shaft, a force transmission mechanism disposed at a first end of the shaft, an end effector disposed at a second end of the shaft, an actuation element that extends along the shaft from the force transmission mechanism to the end effector, and an actuation element guide extending along the shaft. According to an exemplary embodiment, the actuation element guide defines a lumen in which the actuation element guide is received. According to an exemplary embodiment, the actuation element guide is compressed into a pre-compressed state along at least a portion of an axial length of the shaft.

In accordance with at least one exemplary embodiment, a surgical instrument comprises a shaft, a force transmission mechanism disposed at a first end of the shaft, an end effector disposed at a second end of the shaft, an actuation element that extends along the shaft from the force transmission mechanism to the end effector, and an actuation element guide extending along the shaft, a first block, and a second block. According to an exemplary embodiment, the actuation element guide defines a lumen in which the actuation element guide is received. The first block holds a first end of the actuation element guide, according to an exemplary embodiment. The second bock holds a second end of the actuation element guide, according to an exemplary embodiment. The actuation element guide extends along a path that deviates from a straight path between the first and the second block, according to an exemplary embodiment.

In accordance with at least one exemplary embodiment, a method of manufacturing a surgical instrument that comprises a shaft, a force transmission mechanism at a first end of the shaft, an end effector at a second end of the shaft, and an actuation element operably coupling the force transmission mechanism and the end effector, comprises providing an actuation element guide through which the actuation element extends along the shaft. The method further comprises longitudinally compressing the actuation element guide into a pre-compressed state along at least a portion of an axial length of the shaft.

In accordance with at least one exemplary embodiment, a surgical instrument comprises a shaft, a force transmission mechanism disposed at a first end of the shaft, an end effector disposed at a second end of the shaft, an actuation element that extends along the shaft and operably couples the force transmission mechanism and the end effector, and an actuation element guide extending along the shaft. According to an exemplary embodiment, the actuation element guide defines a lumen in which the actuation element guide is received. According to an exemplary embodiment, the force transmission mechanism comprises a flush tube configured to receive a cleaning fluid. The actuation element guide is in flow communication with the flush tube to receive the cleaning fluid in the lumen of the actuation element guide, according to an exemplary embodiment.

In accordance with at least one exemplary embodiment, a method of manufacturing a surgical instrument that comprises a shaft, a force transmission mechanism at a first end of the shaft, an end effector at a second end of the shaft, and an actuation element operably coupling the force transmission mechanism and the end effector, the method comprising providing an actuation element guide that defines a lumen through which the actuation element extends along the surgical instrument shaft. The method further comprises longitudinally compressing the actuation element guide between a first block and a second block of the surgical instrument into a pre-compressed state along at least a portion of an axial length of the shaft, according to an exemplary embodiment. According to an exemplary embodiment, the method further comprises connecting a flush tube to the first block so the first block is in flow communication with the flush tube, the flush tube being configured to receive a cleaning fluid to direct the cleaning fluid into the lumen of the actuation element guide.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
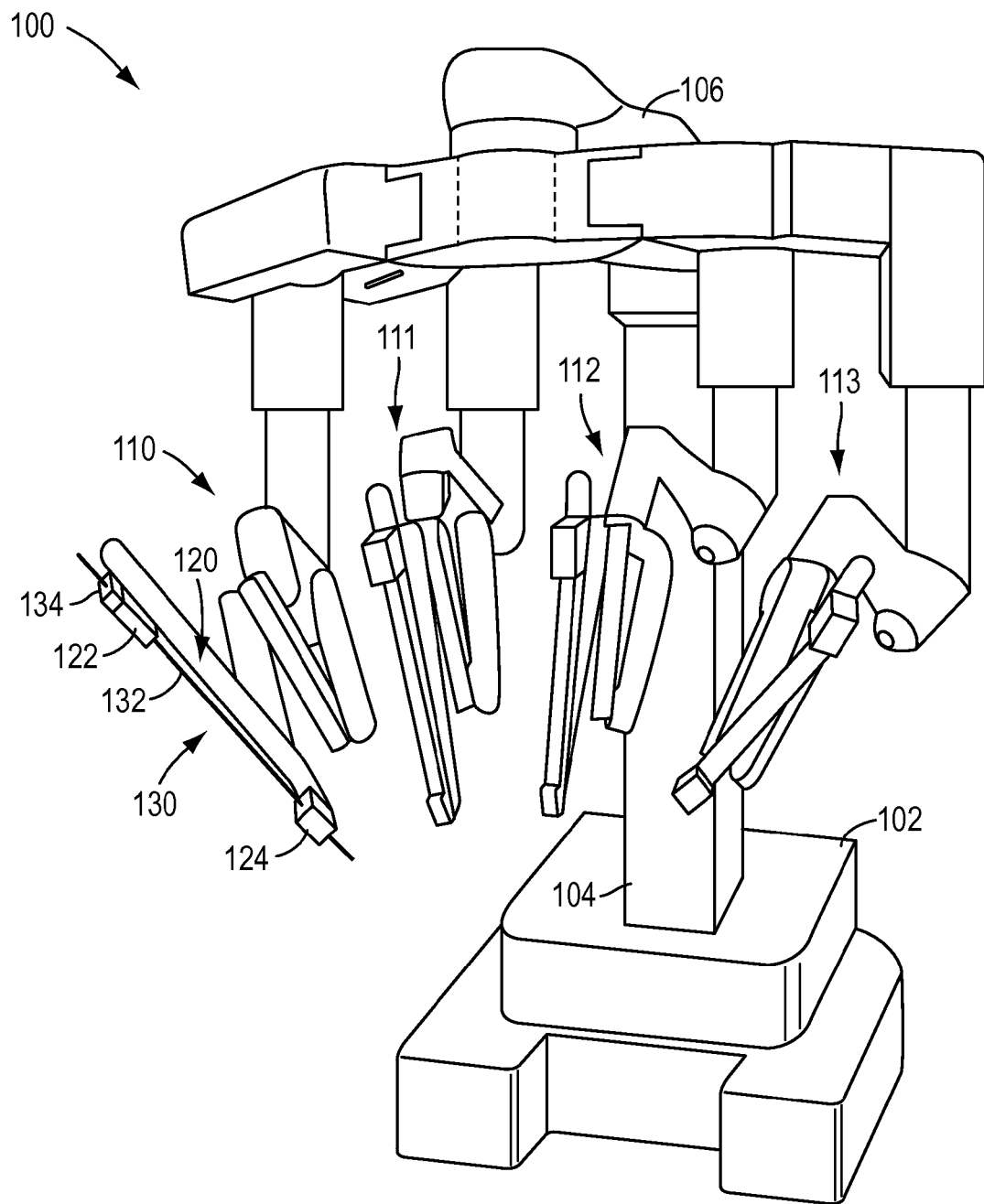
FIG. 1 shows a perspective view of a patient side cart of a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

In this description, an actively flexible piece may be bent by using forces inherently associated with the piece itself. For example, one or more actuation elements (e.g., tendons) may be routed lengthwise along the piece and offset from the piece's longitudinal axis, so that tension on the one or more tendons causes the piece to bend. Other ways of actively bending an actively flexible piece include, without limitation, the use of pneumatic or hydraulic power, gears, electroactive polymers, and the like. A passively flexible piece is bent by using a force external to the piece. An example of a passively flexible piece with inherent stiffness is a plastic rod or a resilient rubber tube. An actively flexible piece, when not actuated by its inherently associated forces, may be passively flexible. A single component may be made of one or more actively and passively flexible portions in series.

In accordance with various exemplary embodiments, the present disclosure contemplates surgical instruments that include actuation element guides configured to compensate for changes in length of actuation elements extending through the actuation element guides. As a result, the actuation element guides may minimize or prevent changes in length in actuation elements, which could otherwise interfere with the functioning of the actuation elements to actuate an instrument, such as, for example, to actuate an end effector and/or wrist of an instrument. In accordance with various exemplary embodiments, at least a portion of an actuation element guide may be compressed into a pre-compressed state. For example, at least a portion of an actuation element guide may be compressed between a first block and a second block. An actuation element guide in a pre-compressed state may have an excess amount of length compared to an actuation element guide following straight path. The present disclosure also contemplates the use of devices to set and/or adjust the compression of the actuation element guide. Various exemplary embodiments further contemplate structures to facilitate reprocessing of instruments that include actuation element guides, including structures that permit flushing of the interior of actuation guide elements.

Referring now to FIG. 1, an exemplary embodiment of a patient side cart 100 of a teleoperated surgical system is shown. A teleoperated surgical system may further include a surgeon console (not shown) for receiving input from a user to control instruments mounted at patient side cart 100. A teleoperated surgical system also can include an auxiliary control/vision cart (not shown), as described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. Further, the exemplary embodiments described herein may be used, for example, with a da Vinci® Surgical System, da Vinci® Si Surgical System, Single Site da Vinci® Surgical System, or a da Vinci® Xi Surgical System, available from Intuitive Surgical, Inc.

Patient side cart 100 includes a base 102, a main column 104, and a main boom 106 connected to main column 104. A plurality of manipulator arms 110, 111, 112, 113 extend from the main boom 106. Manipulator arms 110, 111, 112, 113 may each include an instrument mount portion 120 to which an instrument 130 can be mounted, as illustrated at manipulator arm 110. Manipulator arms 110, 111, 112, 113 can be manipulated during a surgical procedure according to commands provided by a user at the surgeon console. Signal(s) or input(s) can be transmitted from the surgeon to the control/vision cart, which interprets the input(s) and generate command(s) or output(s) that are transmitted to the patient side cart 100. Through drive interface devices and ultimately to the surgical instrument transmission mechanism, an instrument 130 (only one such instrument being mounted in FIG. 1) can be manipulated by the commands.

Instrument mount portion 120 includes an actuation interface assembly 122 and a cannula mount 124. A shaft 132 of instrument 130 extends through a cannula (not shown in FIG. 1) held by cannula mount 124 (and on to a remote site during a surgical or diagnostic procedure), and a force transmission mechanism 134 of instrument 130 connects with the actuation interface assembly 122. Actuation interface assembly 122 includes a variety of drives and other mechanisms that are controlled to respond to input commands at the surgeon console and output drive forces (it should be understood that torque is included in references to forces) to the force transmission mechanism 134 to actuate instrument 130, as those skilled in the art are familiar with. For instance, the input drives of actuation interface assembly 122 can directly engage, or can engage through a sterile interface adapter, with interface structures (not shown) of force transmission mechanism 134 and transmit forces to force transmission mechanism 134 that ultimate actuate the surgical instrument.

Although the exemplary embodiment of FIG. 1 shows an instrument 130 attached to only manipulator arm 110 for ease of illustration, an instrument may be attached to any and each of manipulator arms 110, 111, 112, 113. An instrument 130 may be a surgical instrument with an end effector or may be an endoscopic imaging instrument or other sensing instrument utilized during a surgical procedure to provide information, (e.g., visualization, electrophysiological activity, pressure, fluid flow, and/or other sensed data) of a remote surgical site. Those of ordinary skill in the art will appreciate that the embodiments described herein are not limited to the exemplary embodiment of the patient side cart of FIG. 1 and various other teleoperated surgical system configurations, including patient side cart configurations, may be used.

Figure 2:
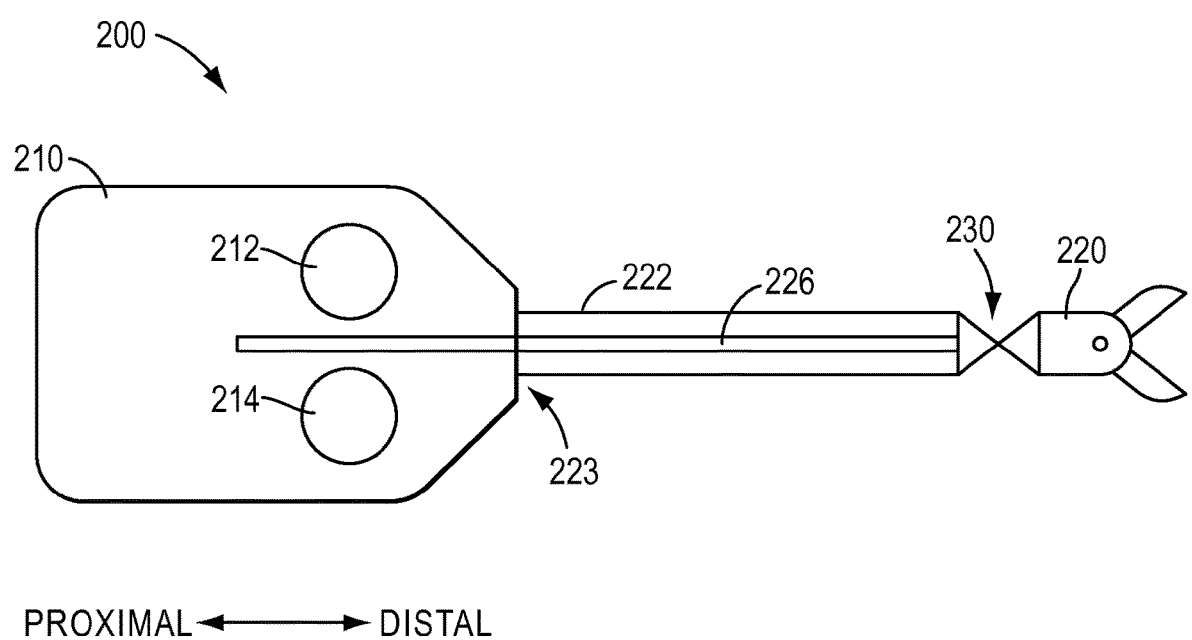
FIG. 2 is a top schematic view of an exemplary embodiment of a surgical instrument including a force transmission mechanism.

FIG. 2 depicts a top view of an exemplary embodiment of a surgical instrument 200 for a teleoperated surgical system. For example, surgical instrument 130 of FIG. 1 may be configured according to the exemplary embodiment of FIG. 2. Surgical instrument 200 includes a force transmission mechanism 210, a shaft 222 connected to force transmission mechanism 210 at a proximal end 223 of shaft 222, and an effector 220 at a distal end of the shaft 222, with relative proximal and distal directions of the surgical instrument being identified in FIG. 2. Instrument 200 also can include a wrist 230 connected to support the end effector 220 at a distal end of shaft 222, although instrument 200 may instead be a non-wristed instrument that lacks a wrist 230. Shaft 222 may be flexible or rigid. Shaft 222 can be sized for minimally invasive surgical procedures. For example, the diameter of shaft 22 can range from about 3 mm to about 15 mm, for example, from about 5 mm to about 8 mm.

Surgical instrument 200 further includes one or more members to translate force between force transmission mechanism 210 and the end effector 220, and to the wrist 230 if any. For instance, one or more actuation element(s) 226 extend from force transmission mechanism 210, through the shaft 222, to end effector 220 to transmit actuation forces. End effector 220 can have a variety of configurations, such as, for example, forceps, a needle driver for suturing, cutting devices, dissecting devices, electrocautery devices, ultrasonic tools, clip appliers, and other end effector configurations for performing various surgical procedures as those having ordinary skill in the art are familiar with. Actuation element(s) 226 may be in the form of tension members, such as when force transmission mechanism 210 is a pull-pull mechanism, or one or more rods, such as when force transmission mechanism 210 is a push-pull mechanism, as described in U.S. Pat. No. 8,545,515, which is hereby incorporated by reference in its entirety.

Force transmission mechanism 210 may include one or more components to engage with a patient side cart of a teleoperated surgical system to transmit a force provided by the patient side cart to surgical instrument 200. According to an exemplary embodiment, force transmission mechanism 210 may include one or more actuation input mechanisms 212, 214 that engage with a manipulator of a patient side cart, such as actuation interface assembly 122 of patient side cart 100, as discussed above in regard to the exemplary embodiment of FIG. 1.

Figure 3:
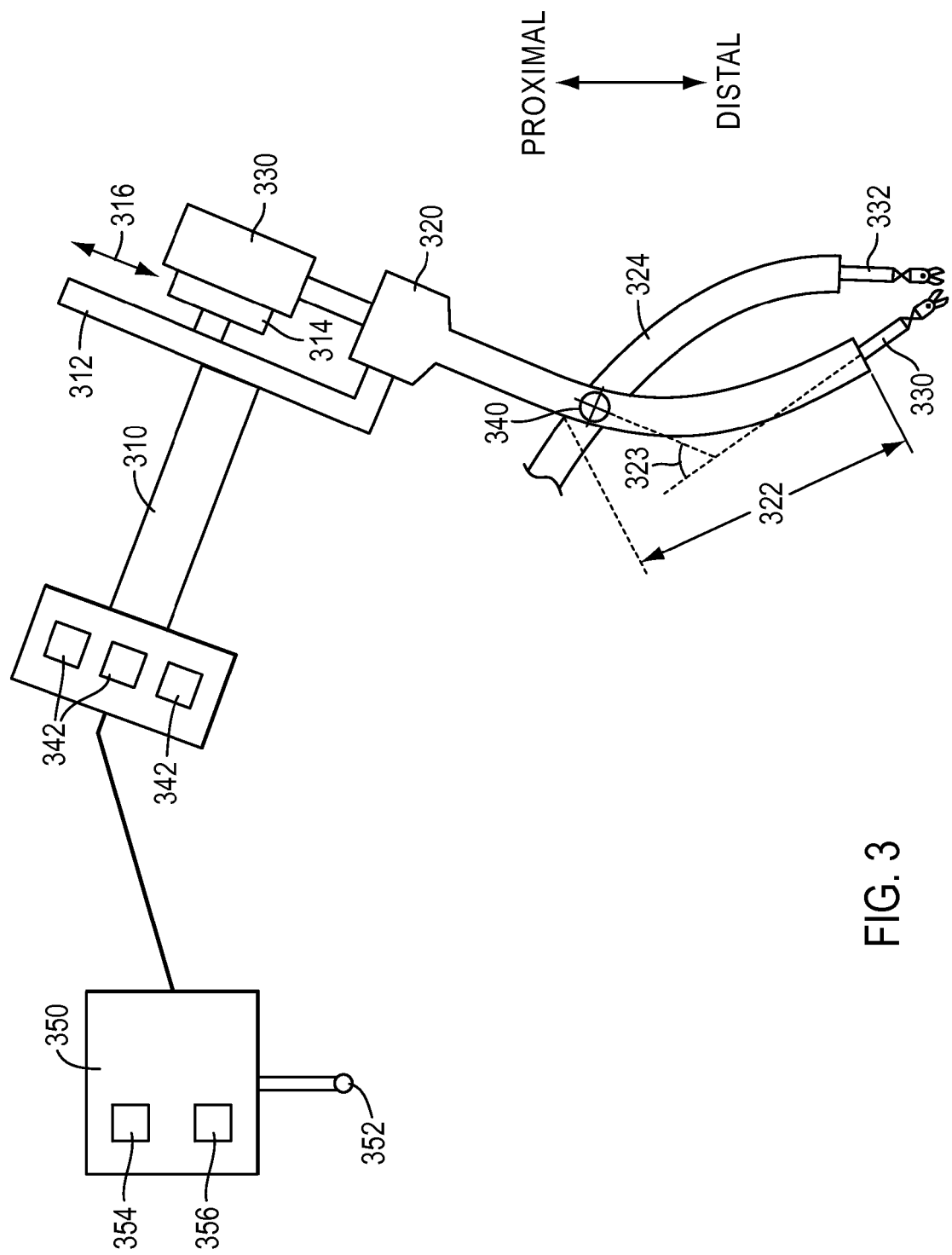
FIG. 3 is a side schematic view of surgical instrument mounted to a patient side cart and inserted into a cannula with a curved section, according to an exemplary embodiment.

Turning to FIG. 3, a side view is shown of a cannula 320 coupled to a manipulator arm 310 of a patient side cart, such as one of manipulator arms 110-113 of the patient side cart 100 of the exemplary embodiment of FIG. 1. Cannula 320 may be connected to a spar 312 of manipulator arm 310 (e.g., via cannula mount 124 in the exemplary embodiment of FIG. 1). An instrument 330 may be coupled to a carriage 314 of spar 312. Carriage 314 can include an actuation interface assembly (not shown) to couple with a force transmission mechanism (not shown) of instrument 330 (e.g., by coupling force transmission mechanism 134 to actuation interface assembly 122 of the exemplary embodiment of FIG. 1.). Carriage 314 may be configured to move linearly along spar 312 in the direction indicated by arrows 316 in FIG. 3, which causes the surgical instrument 330 to be inserted and withdrawn through cannula 320. Although cannula 320 is depicted as being connected to carriage 314 and spar 312 of manipulator arm 310, the various exemplary embodiments described herein are not limited to teleoperated surgical instruments and may also regard manual (e.g., hand operated) surgical instruments and curved cannulas not mounted to a teleoperated surgical system.

Teleoperated actuation forces (it should be understood that torque is included in references to forces) from various motors 342 may respectively control a degree of freedom (DOF) of instrument 330 and keep a remote center of motion 340 stationary with regard to a reference frame, such as a body wall of a patient so trauma to tissue is minimized. Although three motors 342 are shown in the exemplary embodiment of FIG. 3, manipulator arm 310 may include other numbers of motors 342. Teleoperated control of manipulator arm 310 is conducted via a master control unit 350, schematically depicted in the exemplary embodiment of FIG. 3, which may be a surgeon's console of a teleoperated surgical system. Master control unit 350 may include a master input 352 that receives an operator's input to control associated slave manipulator arm 310 and its instrument 330. Master control unit 350 includes a memory 354 that includes non-transitory instructions that are executed by processing/control system 356 (i.e., that contains a logic unit, such as an adder) to control motion of manipulator arm 310 and its associated instrument 330.

Cannula 320 may include a curved section 322. In other words, at least a section of the cannula 320 may have a curved longitudinal axis. Curved section 322 may have a curvature with an angle 323 between ends of section 322 ranging from, for example, about 40° to about 65°. In another example, curved section 322 may have a curvature ranging from about 45° to about 60°. When two or more curved cannulas, such as cannulas 320 and 324 in the exemplary embodiment of FIG. 3, are positioned so the curved sections of the cannulas are generally offset from each other, triangulation (e.g., the ability for the distal ends of two surgical instruments to be positioned along two legs of a triangle to work effectively at a surgical site located at the apex of the triangle) of the cannulas and instruments can be achieved. Cannula 324 is partially depicted in the exemplary embodiment of FIG. 3 without attachment to a manipulator arm but, similarly to cannula 320, attaches to a different manipulator arm than arm 310. Further, using cannulas with curved sections facilitates insertion of the cannulas through a single aperture (e.g., incision, port, natural orifice, or other aperture) in a patient's body. Arranging cannulas 320, 324 in a triangulation configuration facilitates viewing a surgical site and utilizing instruments 330, 332 at the surgical site.

As discussed above, a shaft of a surgical instrument (e.g., shaft 222 of the exemplary embodiment of FIG. 2) can be flexible, such as to facilitate insertion and withdrawal of an instrument through a curved section of a cannula. The instrument shaft also has a degree of stiffness so the shaft may support an end effector, such as when the distal end of the shaft and the end effector are extended beyond a distal end of the curved cannula. General examples of passively flexible instruments are described in U.S. Pat. No. 8,545,515 (entitled "Curved Cannula Surgical System"), issued Oct. 1, 2013, and U.S. Provisional Patent Application No. 61/866,367 (entitled "Instrument Shaft for Computer-Assisted Surgical System"), filed Aug. 15, 2013, each of which is hereby incorporated by reference herein in its entirety. When the flexible shaft of an instrument is inserted and withdrawn through the curved section of a cannula, the shaft and components within the shaft, such as actuation elements, are bent. Bending may have an effect upon the actuation elements. For instance, bending may cause a change in length of an actuation element, depending upon whether the actuation element is located on an inside of a curve of bending (which could lead to a negative change in length of the actuation element) or on an outside of the curve of bending (which could lead to a positive change in length of the actuation element).

Actuation Element Guides for Actuation Elements of Surgical Instruments

Various exemplary embodiments described herein contemplate guides for actuation elements of a surgical instrument. Actuation element guides of the various exemplary embodiments described herein may direct actuation elements along a length of a surgical instrument. For example, actuation element guides may provide pathways for actuation elements guides through a shaft of a surgical instrument. The actuation element guides may also provide a degree of support for actuation elements, such as by increasing a buckling strength of the actuation elements. Various exemplary embodiments described herein contemplate actuation element guides that have a non-linear shape along at least a portion of its length when a shaft including the actuation element guides is straight. By using actuation element guides having a non-linear shape, according to the various exemplary embodiments described herein, changes in length of an actuation element extending through the guide, which may result from bending an instrument shaft including the guide through a curved section of a cannula, may be accommodated.

Figure 4:
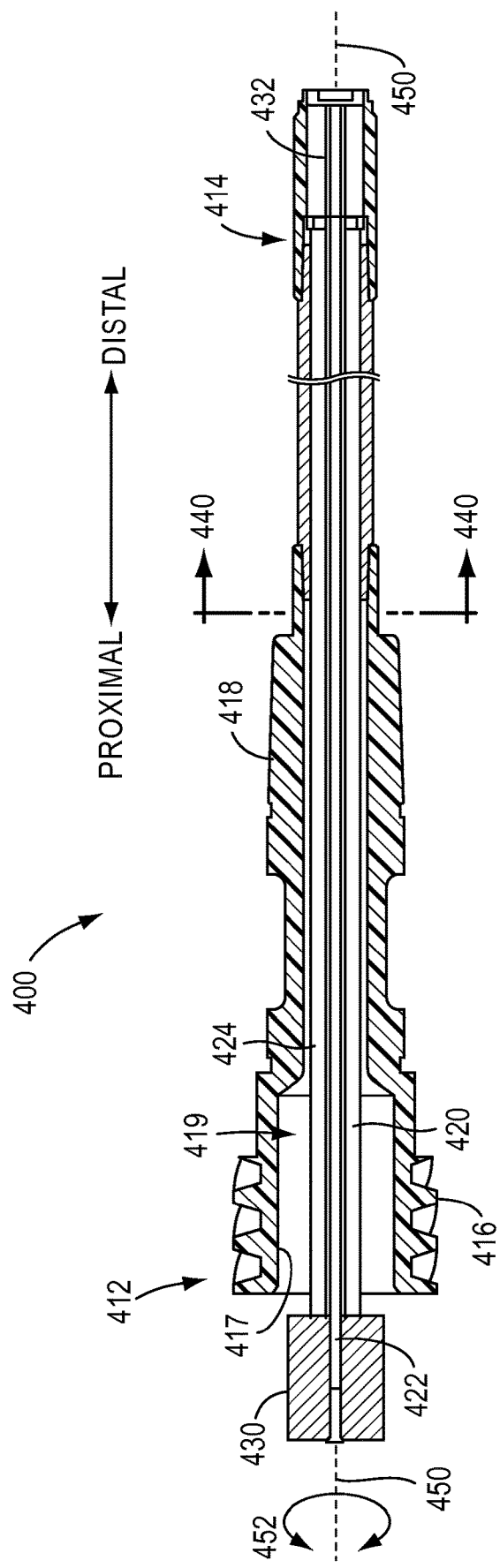
FIG. 4 is a longitudinal cross-sectional view of a shaft for a surgical instrument, with components disposed internal to the shaft being shown, according to an exemplary embodiment.

Turning to FIG. 4, a cross-sectional view is shown of a shaft 400 of a surgical instrument, according to an exemplary embodiment. Shaft 400 may have a proximal portion 412 and a distal portion 414, and include one or more actuation element guides 420, 422, 424 that extend between proximal portion 412 and distal portion 414 of shaft 400. As shown in the exemplary embodiment of FIG. 4, actuation element guide 422 may be held between a proximal block 430 disposed at proximal portion 412 of shaft 400 and a distal block 432 disposed at distal portion 414 of shaft 400. According to an exemplary embodiment, proximal block 430 may be fixed to a force transmission mechanism (e.g., force transmission mechanism 210 of FIG. 2), as will be discussed below. Other actuation element guides, such as actuation element guides 420 and 424, also may be held between blocks 430 and 432.

As mentioned above, instrument shaft 400 may have a rolling degree of freedom, such that shaft 400 is able to rotate about its longitudinal axis. According to an exemplary embodiment, shaft 400 may include gear teeth 416 to mesh with a roll input gear (not shown) or other mechanism of a force transmission mechanism (e.g., force transmission mechanism 210 of FIG. 2) to induce a rolling motion for shaft 400, such as to roll shaft 400 along the directions indicated by arrows 452 about longitudinal axis 450 in the exemplary embodiment of FIG. 4. Distal block 432 is connected to a distal portion 414 of shaft 400 in a fixed manner so that distal block 432 rolls as shaft 400 is rolled. As shown, actuation element guides 420, 422, 424 are fixed to distal block 432 and to proximal block 430 so as to compress actuation element guides 420, 422, 424 into a pre-compressed state between proximal block 430 and distal block 432. As a result, actuation element guides 420, 422, 424 roll when shaft 400 is rolled. Actuation element guides 420, 422, 424 can roll together as a single unit with shaft 400, or alternatively, one or more actuation element guides 420, 422, 424 can roll independently of one another.

According to an exemplary embodiment, actuation element guides 420, 422, 424 are configured to rotate relative to at least one of blocks 430, 432. For example, proximal block 430 may be fixed to a force transmission mechanism of an instrument (e.g., fixed to force transmission mechanism 210 of the exemplary embodiment of FIG. 2) while shaft 400, distal block 432, and actuation element guides 420, 422, 424 are rotatable (e.g., roll) about axis 450 relative to the force transmission mechanism. As a result, actuation element guides 420, 422, 424 are held by proximal block 430 while also being rotatable relative to proximal block 430. In some cases, rotation of the actuation element guides 420, 422, 424 relative to fixed proximal block 430 results in twisting of at least a portion of actuation element guides 420, 422, 424.

Proximal block 430 may be made of a material to minimize wear due to the rotational motion between actuation element guides 420, 422, 424 and proximal block 430. For example, proximal block 430 may be made of an anti-galling material, such as, for example, Nitronic® 60 alloy, which is distributed by High Performance Alloys. According to an exemplary embodiment, either or both of blocks 430, 432 may be made of, for example, a plastic material, a metal, a combination of a plastic material and a metal, or other surgical instrument materials familiar to one of ordinary skill in the art. For example, block 430 and/or block 432 may be made of polyether ether ketone (PEEK).

The present disclosure contemplates configurations other than those described above for FIG. 4. For example, actuation element guides 420, 422, 424 may be rotatable relative to both distal block 432 and proximal block 430. As a result, when shaft 400 and proximal block 430 are rolled, actuation element guides 420, 422, 424 remain stationary relative to shaft 400 and block 430. In another exemplary embodiment, actuation element guides 420, 422, 424 are compressed between proximal and distal blocks 430, 432, but actuation element guides 420, 422, 424 also pass through proximal block 430 into a force transmission mechanism (e.g., force transmission mechanism 210 of FIG. 2) where actuation element guides 420, 422, 424 are fixed. Further, distal block 432 may be rotatable relative to actuation element guides 420, 422, 424 since actuation element guides 420, 422, 424 are fixed to the force transmission mechanism.

Shaft 400 may be a flexible hollow body 418 through which actuation element guides 420, 422, 424 extend. According to an exemplary embodiment, hollow body 418 may define an inner wall 417. The portion of hollow body 418 defining inner wall 417 may be a continuous surface along the axial length of shaft 400 (e.g., along the proximal-distal direction of shaft 400). An open space 419 is provided between inner wall 417 of hollow body 418 and actuation element guides 420, 422, 424, so as to provide space for other instrument components that extend through shaft 400 (e.g., one or more flux conduits to convey, for example, electrical energy, fluid, suction, and other fluxes used by surgical instruments). Actuation element guides (e.g., actuation guide elements 420, 422, 424) held between proximal block 430 and distal block 432 may be unconstrained (e.g., not in contact with support structures to direct or support guides) between those blocks. For instance, open space 419 may be located between actuation element guides 420, 422, 424 and between guides 420, 422, 424 and inner wall 417 of hollow body 418. The open space 419 within hollow body 418 provides an unconstrained configuration for actuation element guides 420, 422, 424, which permits actuation element guides 420, 422, 424 to move freely within hollow body 418. Such a configuration can facilitate compensating for changes in the length of guides 420, 422, 424, as will be discussed in further detail below.

According to an exemplary embodiment, actuation elements may be primarily supported along shaft 400 by actuation element guides 420, 422, 424 instead of hollow body 418 due to the limited contact between hollow body 418 and actuation element guides 420, 422, 424. This is further illustrated in the exemplary embodiment of FIG. 5, which is a cross-sectional view of a surgical instrument shaft 500, which may be a cross-section located along line 440-440 of FIG. 4. As shown in the exemplary embodiment of FIG. 5, shaft 500 may comprise a hollow body 510 through which actuation element guides 520-525 may extend, with actuation elements 530-535 (e.g., pull/pull tension elements) respectively extending through an interior of actuation element guides 520-525. Hollow body 510 and actuation element guides 520-525 may be configured so that open space 514 is provided between an interior wall 511 of hollow body 510 and actuation element guides 520-525, as described above.

A surgical instrument shaft can be made of materials that provide the shaft with flexibility, such as to facilitate bending of the shaft when inserting and withdrawing the shaft, for example, through a curved section of a cannula. However, a surgical instrument shaft also can be made of materials that provide the shaft with sufficient stiffness, for example, to support an end effector of the surgical instrument when a distal portion of the instrument including the end effector is extended beyond a distal end of a cannula. For example, hollow body 510 may be made of PEEK, according to an exemplary embodiment. The PEEK may include one or more fillers, such as, for example, glass fiber reinforcement or carbon fiber reinforcement. According to an embodiment, a material used for a shaft may include a material to increase the lubricity of the shaft. For instance, the material of the shaft may include, for example, about 5% to about 10% of PTFE and/or perfluoropolyether (PFPE).

A surgical instrument shaft also can include additional layers and/or materials. For example, shaft 500 may further include an outer layer 512 (e.g., a sheath), as shown in the exemplary embodiment of FIG. 5. Outer layer 512 may comprise, for example, a lubricious material to facilitate insertion and withdrawal of shaft 500 through a cannula. Outer layer 512 may comprise, for example, ethylene tetrafluoroethylene (ETFE) or other shaft materials familiar to one of ordinary skill in the art. The outer layer 512 of ETFE may be, for example, heat shrunk onto hollow body 510. However, a shaft 600 of a surgical instrument may include only a hollow body 610 without additional layers, as shown in the exemplary embodiment of FIG. 6, which also depicts actuation element guides 620-625 and actuation elements 630-635 extending through hollow body 610. Hollow body 610 may be made of, for example, PEEK, PEEK comprising one or more filler, or other shaft materials familiar to one of ordinary skill in the art.

Figure 5:
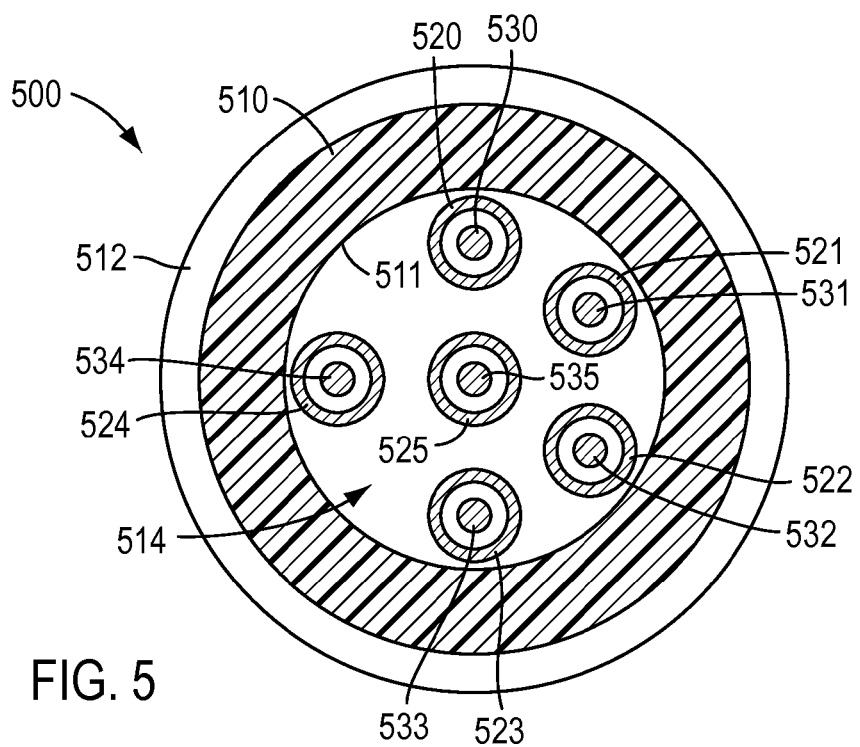
FIG. 5 is a transverse cross-sectional view of a surgical instrument shaft with a sheath, according to an exemplary embodiment.
Figure 6:
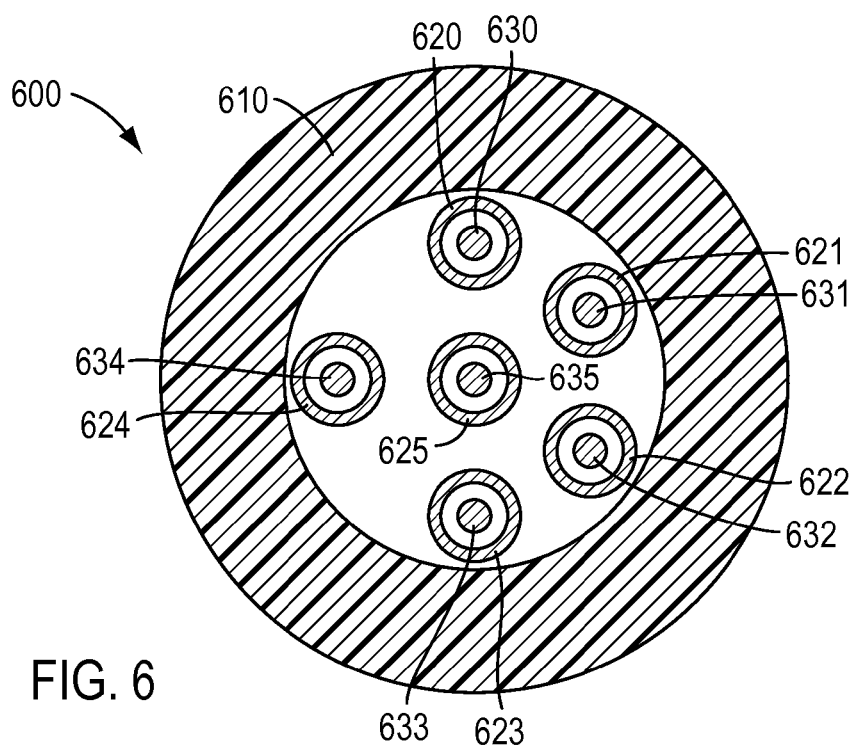
FIG. 6 is a transverse cross-sectional view of a surgical instrument shaft, according to an exemplary embodiment.

With reference to the exemplary embodiments of FIGS. 5 and 6, the surgical instrument includes six actuation element guides 520-525, 620-625 for receiving six actuation elements 530-535, 630-635. The six actuation elements 530-535, 630-635 may be used to actuate, for example, an end effector (such as end effector 220 of the exemplary embodiment of FIG. 2) and a wrist (such as wrist 230 of the exemplary embodiment of FIG. 2). According to an exemplary embodiment, two of actuation elements 530-535, 630-635 can actuate an end effector, such as when actuation elements 530-535, 630-635 are pull/pull type tension elements. Further, four of actuation elements 530-535, 630-635 can actuate a wrist. Of course those having ordinary skill in the art would appreciate that other numbers and arrangements of actuation elements may be provided without departing from the scope of the present disclosure.

Figure 7:
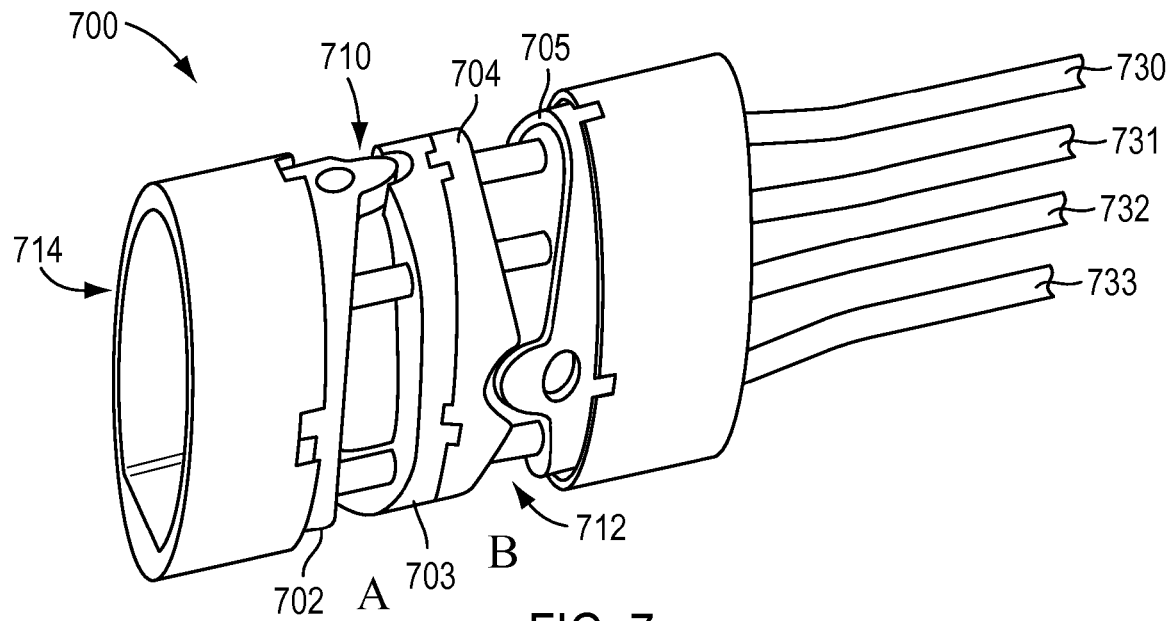
FIG. 7 is a perspective, isolated view of a wrist and actuation elements for a surgical instrument, according to an exemplary embodiment.

Turning to FIG. 7, an exemplary embodiment of a wrist 700 is shown that may be used with the various exemplary embodiments described herein. Wrist 700 includes a series of links 702-705 coupled to one another to provide joints 710 and 712 that permit wrist 700 to bend in pitch and yaw directions when actuation elements 730-733 are tensioned to actuate wrist 700. The pitch and yaw directions may be arbitrary rotational motions about orthogonal axes in a Cartesian reference system. Thus, wrist 700 may be a two stage (AB) wrist with two physical pivots at joints 710 and 712, so there are two DOFs for wrist 700, namely a pitch DOF (A) and a yaw DOF(B). Wrist 700 can have, for example, a range of motion of about +/−45 degrees for each joint 710, 712, according to an exemplary embodiment. By using a wrist with few joints, such as wrist 700, a relatively small number of actuation elements, such as four actuation elements 730-733 in the exemplary embodiment shown, may be used. As a result, additional free space may be used within a surgical instrument shaft for other instrument components, including, for example, actuation element guides that may be permitted to move within the open space of a hollow body of the shaft.

Figure 8:
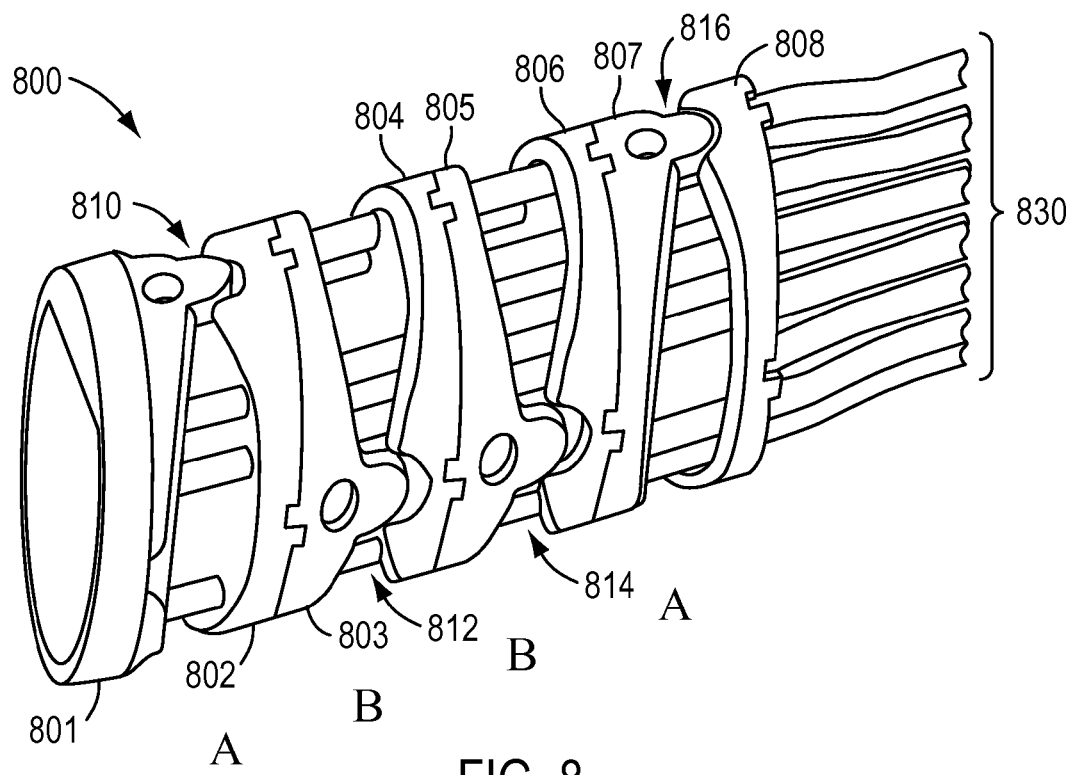
FIG. 8 is a perspective, isolated view of a wrist and actuation elements for a surgical instrument, according to another exemplary embodiment.

Although a wrist with 2 DOFs may be used, such as wrist 700, other wrist configurations may be used with the various exemplary embodiments described herein. For example, wrist 800 of the exemplary embodiment of FIG. 8 may be used. Wrist 800 comprises disks 801-808 coupled to one another to provide four joints 810, 812, 814, 816. Adjacent links of wrist 800 may pivot about joints 810, 812, 814, 816 when actuation elements 830 are tensioned so as to bend wrist 800 about arbitrary pitch and yaw directions. Thus, wrist 800 may be a four stage wrist (e.g., ABBA type wrist or other combinations of pitch and yaw) with 4 DOFs. Wrist 800 may have a greater range of motion than wrist 700 but require a larger number of actuation elements 830 (e.g., eight actuation elements 830) to actuate and bend wrist 800 via joints 810, 812, 814, 816. According to an exemplary embodiment, wrist 800 may be used and configured according to the various exemplary embodiments described in U.S. Pub. No. US 2012/0215220 (entitled "Fusing and Cutting Surgical Instrument and Related Methods"), published on Aug. 23, 2012, which is hereby incorporated by reference in its entirety. According to an exemplary embodiment, wrist 800 has a range of motion of about +/−80 degrees to about +/−90 degrees for each degree of freedom of wrist 800. In general, increasing the number of actuation elements leads to more space being taken up within the instrument shaft due to the space required for increasing the number of actuation elements.

The various exemplary embodiments described herein also can include wrist configurations as described in U.S. Pat. No. 6,817,974, entitled "Surgical Tool Having Positively Positionable Tendon-Actuated Multi-Disk Wrist Joint" and issued on Nov. 16, 2004, and U.S. Pat. No. 7,320,700, entitled "Flexible Wrist for Surgical Tool" and issued on Jan. 22, 2008, each of which is incorporated by reference herein in its entirety.

Actuation elements of the various exemplary embodiments described herein may extend along a 180 degree turn at a distal end of a wrist. For example, actuation element 730 of the exemplary embodiment of FIG. 7 may follow a 180 degree turn at distal end 714 of wrist 700 and extend back along wrist as actuation element 731. In another example, each of the actuation elements may terminate at a distal end of wrist and be coupled to the distal end of the wrist. For example, each of actuation elements 730-733 may terminate at distal end 714 of wrist 700 and be coupled to distal end 714, such as via crimps (not shown).

Actuation element guides may be structures to support and guide actuation elements along a desired path through a shaft of a surgical instrument. According to an exemplary embodiment, actuation element guides may be hollow tubes, such as actuation element guides 520-525, 620-625 in the exemplary embodiments of FIGS. 5 and 6. The hollow tubes may be made of a material that permits the hollow tubes to be flexible and bend, but also that provides a degree of stiffness so as to support actuation elements extending through the interior of the hollow tubes. According to an exemplary embodiment, the hollow tubes may be made of stainless steel or other surgical instrument material. For example, suitable materials include, but are not limited to, type 304 stainless steel, 17-7 stainless steel, and/or type 316 stainless steel, or other stainless steel alloys familiar to one of ordinary skill in the art. According to another exemplary embodiment, the hollow tubes may be made of a nickel-titanium alloy (e.g., a Nitinol alloy), or a polymer, such as, for example PEEK or other polymers familiar to one of ordinary skill in the art.

Figure 9:
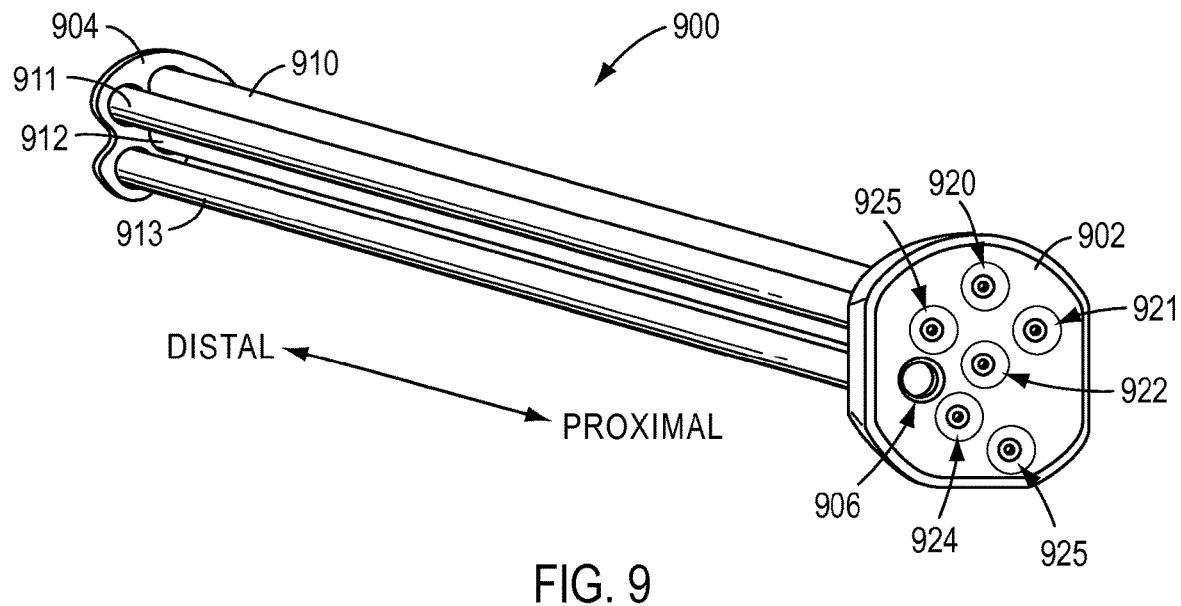
FIG. 9 is a perspective view of a tube bundle for a surgical instrument, according to an exemplary embodiment.

Turning to FIG. 9, a bundle 900 of actuation element guides is shown extending between a proximal block 902 and a distal block 904. Actuation element guides of various exemplary embodiments described herein, such as actuation element guides 420, 422, 424 of FIG. 4, may be configured according to the hollow tubes of bundle 900 of the exemplary embodiment of FIG. 9. The hollow tubes of bundle 900 may have solid walls defining continuous inner surfaces along their axial length (e.g., between proximal block 902 and distal block 904), according to an exemplary embodiment. According to an exemplary embodiment, the hollow tubes of bundle 900 may be unconstrained (e.g., not in contact with support structures to direct or support guides) between proximal block 902 and distal block 904, as discussed above with regard to the exemplary embodiment of FIG. 4.

Although only four hollow tubes 910-913 are visible in the exemplary embodiment of FIG. 9, bundle 900 may include various numbers of hollow tubes. For instance, bundle 900 may include six hollow tubes (two of which are hidden from view in FIG. 9), with apertures 920-925 for the ends of the hollow tubes located in proximal block 902 to receive actuation elements (not shown) to extend through the hollow tubes. However, bundle 900 may comprise other numbers of hollow tubes, such as, for example, one, two, three, four, five, seven, eight, nine, ten, or more hollow tubes.

According to an exemplary embodiment, proximal block 902 includes an aperture 906 to receive cleaning fluid that is distributed to the various hollow tubes for cleaning purposes, as will be described below. Distal block 904 includes a corresponding number of apertures (not shown) for the hollow tubes as proximal block 902. Hollow tube bundle 900 may be used in the various exemplary embodiments described herein, such as by extending the hollow tubes of bundle 900 between proximal block 430 and distal block 432 of the exemplary embodiment of FIG. 4 (e.g., bundle 900 can include actuation element guides 420, 422, 424 of FIG. 4).

As discussed above, bending a shaft of a surgical instrument, such as when a surgical instrument extends through a curved section of a cannula, may result in a change of length of actuation elements extending through the shaft. To compensate for such changes in length, actuation element guides may have a non-linear shape, when a shaft including the actuation element guides is straight (e.g., before the shaft is bent and/or actuation forces are applied to actuation elements), along at least a portion of the length of the actuation element guides. According to an exemplary embodiment, an actuation element guide may be pre-compressed (e.g., in a pre-compressed state, such as, for example, before the shaft including the actuation element guide is bent and/or actuation forces are applied to actuation elements) to accomplish a non-linear shape along at least a portion of the length of the actuation element guide when a shaft including the actuation element guides is straight. For example, actuation element guides 420, 422, 424 in the exemplary embodiment of FIG. 4 may be coupled to proximal block 430 and distal block 432 such that actuation element guides 420, 422, 424 are pre-compressed between block 430 and block 432. According to an exemplary embodiment, the pre-compression force on the actuation element guides 420, 422, 424 can range, for example, from about 1 pound (lbf) to about 15 pounds (lbf), for example the pre-compression force may range from about 1 pound (lbf) to about 10 pounds (lbf). In another example, tubes 910-913 in the exemplary embodiment of FIG. 9, which may function as actuation element guides, can be coupled to proximal block 902 and distal block 904 such that tubes 910-913 are pre-compressed between proximal block 902 and distal block 904.

Figure 10:
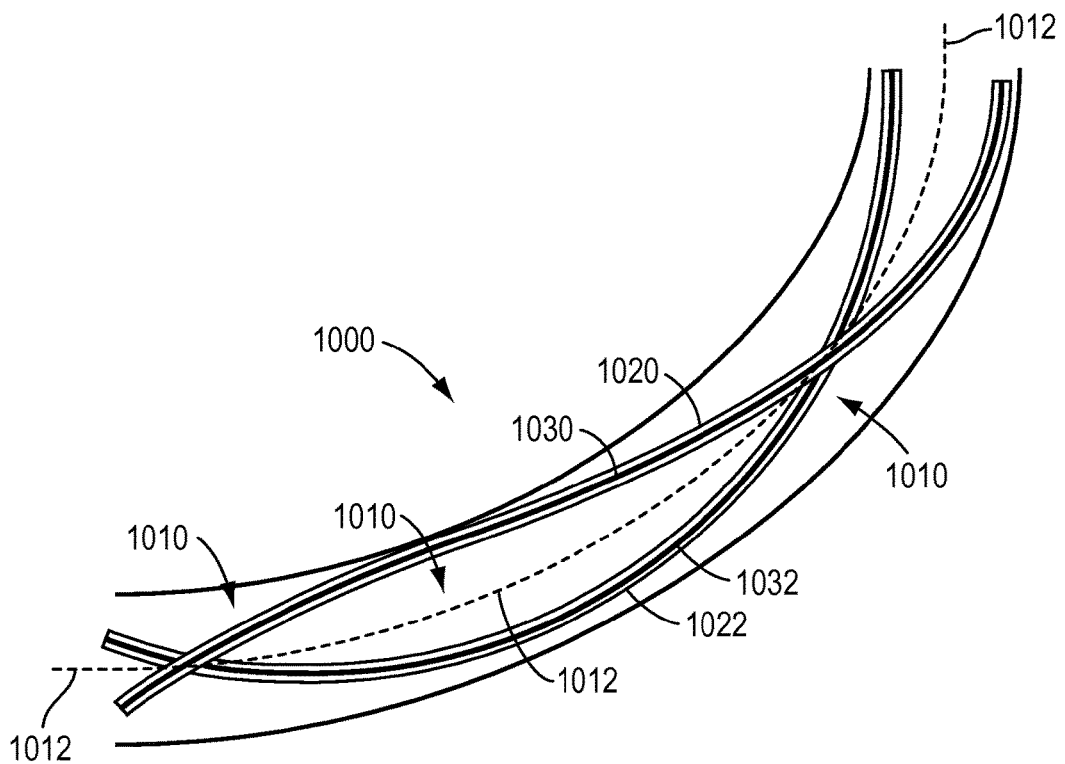
FIG. 10 is a schematic cross-sectional view of an instrument shaft including actuation element guides, according to an exemplary embodiment.

Turning to FIG. 10, an instrument shaft 1000 is schematically shown in a bent configuration to demonstrate how actuation element guides of the various exemplary embodiments described herein function to compensate for changes in length of actuation elements. For example, the actuation element guides of FIGS. 4 and 9 and the following embodiments described below may be configured according to the exemplary embodiment of FIG. 10 (e.g., the exemplary embodiments described herein may be bent into the configuration shown in FIG. 10 and function in the same manner). Shaft 1000 may be a flexible shaft, such as, for example, shaft 400 of the exemplary embodiment of FIG. 4, which has been bent, such as by extending shaft 1000 through a curved portion of a cannula (e.g., through curved portion 322 of cannula 320 in the exemplary embodiment of FIG. 3). Actuation element guides 1020, 1022 extend through an interior of shaft 1000, with actuation elements 1030, 1032 respectfully extending through guides 1020, 1022. Actuation element guides 1020, 1022 may be configured according to the various exemplary embodiments described herein, such as, for example, guides 420, 422, 424 in FIG. 4 or bundle 900 in FIG. 9.

As depicted in the exemplary embodiment of FIG. 10, actuation element guides 1020, 1022 can have a non-linear shapes along at least a portion of the lengths of actuation element guides 1020, 1022 (e.g., along a longitudinal axis of actuation element guides 1020, 1022). For example, actuation element guides 1020, 1022 have non-linear shapes when shaft 1000 is straight. In this way, when shaft 1000 is straight, actuation element guides 1020, 1022 have excess length (e.g., relative to a guide following a straight path from one end of shaft 1000 to the other) so that guides 1020, 1022 are not straight (e.g., non-linear) along at least a portion of the lengths of guides 1020, 1022. In other words, actuation element guides 1020, 1022 extend along a path that deviates from a straight path between first and second blocks. To provide actuation element guides 1020, 1022 with non-linear shapes, actuation element guides 1020, 1022 are pre-compressed between blocks (not shown) at opposite ends of actuation element guides 1020, 1022, as discussed above with regard to the exemplary embodiments of FIGS. 4 and 9.

The shafts and actuation element guides of the various exemplary embodiments described herein may be designed to compensate for changes in length of actuation elements, such as, for example, changes in length due to bending, rolling and/or twisting motions of actuation element guides.

By compensating for changes in length of actuation elements, the various exemplary embodiments described herein may minimize or prevent change in length of the actuation elements, which could otherwise degrade the efficacy of actuation elements to actuate a surgical instrument. For instance, because actuation element guides 1020, 1022 are pre-compressed, actuation element guides 1020, 1022 have excess length relative to a longitudinal axis 1012 of shaft 1000 when shaft 1000 is straight, such as, for example, when shaft 1000 does not extend through a curved portion of a cannula. According to an exemplary embodiment, actuation element guides 1020, 1022 are pre-compressed by an amount so that even under a maximum amount of bending, such as when shaft 1000 is inserted through a cannula curved section with the greatest degree of bending, actuation elements guides 1020, 1022 will remain pre-compressed with an excess amount of length. According to an exemplary embodiment, because actuation elements 1030, 1032 extend through and are guided by actuation element guides 1020, 1022, actuation elements 1030, 1032 also have an excess amount of length. Further, shaft 1000 may be a hollow shaft that provides open space 1010 within shaft 1000, so that actuation element guides 1020, 1022 are unconstrained by shaft 1000 along at least a portion of the length of actuation element guides 1020, 1022. As a result, actuation element guides 1020, 1022 may move relative to shaft 1000 and/ additional components may extend through shaft 1000, as discussed above with regard to the exemplary embodiment of FIG. 4.

According to an exemplary embodiment, when actuation elements 1030, 1032 experience a negative change in length, such as due to bending of shaft 1000 and at least a portion of actuation elements 1030, 1032 being disposed on an inside of a curve of bending, the excess length of actuation element guides 1020, 1022 due to the pre-compressed shapes of actuation element guides 1020, 1022 compensates for the negative change in length. Thus, when actuation elements 1030, 1032 experience a positive change in length, such as due to bending of shaft 1000 and at least a portion of actuation elements 1030, 1032 being disposed on an outside of the curve of bending, actuation elements guides 1020, 1022 may be unconstrained within open space 1010 to permit actuation element guides 1020, 1022 to move relative to shaft 1000. Thus, designing actuation element guides 1020, 1022 to be pre-compressed and unconstrained within open space 1010 of shaft 1000 permits the guides 1020, 1022 to move relative to shaft 1000 so that the positive change in length due to bending may be absorbed and effects of change in length upon actuation elements 1030, 1032 may be minimized or avoided.

Various exemplary embodiments herein can compensate for changes in length of actuation elements at any orientation of an instrument relative to a curved portion of a cannula. In other words, a particular instrument orientation relative to a curved portion of a cannula is not required (e.g., angular rotation relative to a longitudinal axis of the instrument, such as a roll angle relative to a longitudinal axis of an instrument). For example, when the curvature of curved section 322 of cannula 320 in the exemplary embodiment of FIG. 3 lies in a single plane, instruments including actuation element guides according to the various exemplary embodiments described herein do not need to be inserted into cannula 320 so the instrument, and an actuation element guide within the instrument, is oriented at a particular angle relative to the plane of curvature in order for the actuation element guide to be able to compensate for changes in length of an actuation element extending within the actuation element guide. Instead, the configurations (e.g., excess length of guides and/or open space within shafts) permit the actuation element guides to compensate for changes in length of actuation elements at any orientation relative to the curvature of a cannula.

Figure 11:
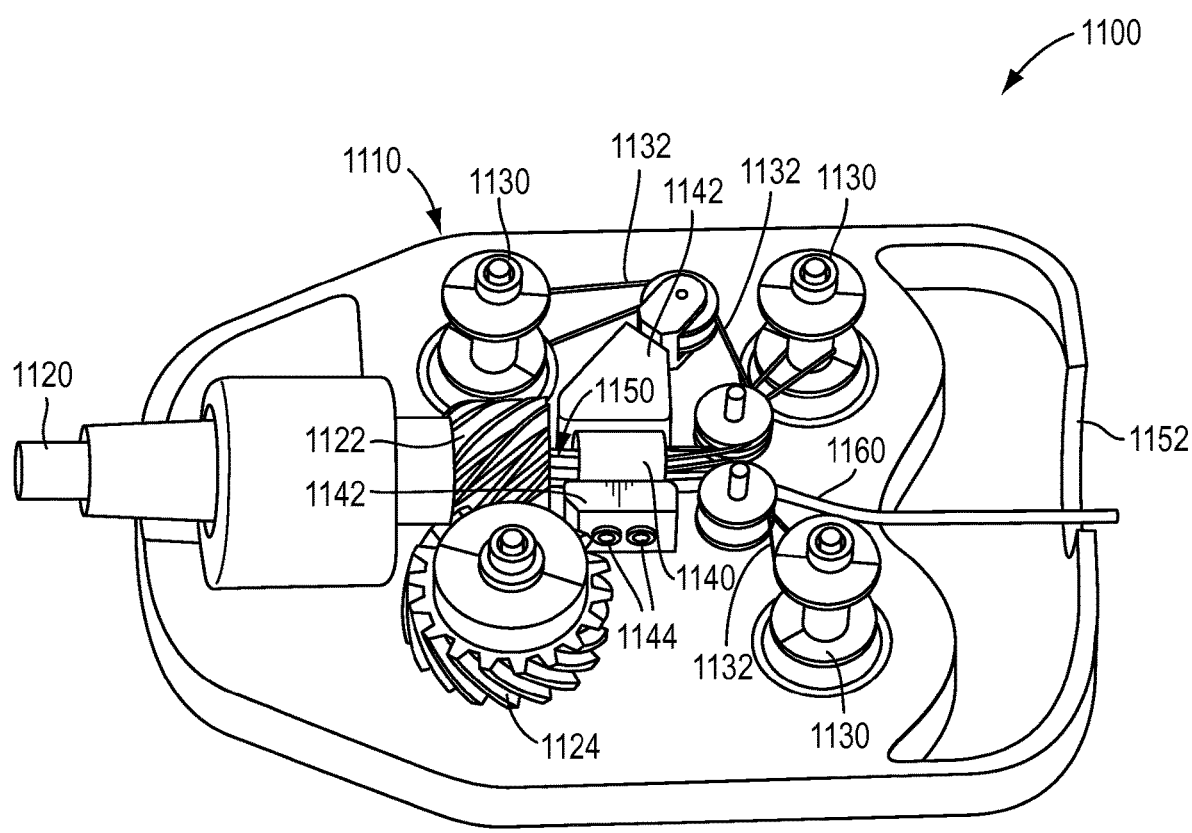
FIG. 11 is a perspective view of internal components of a force transmission mechanism including a mounted block to hold actuation element guides, according to an exemplary embodiment.

The present disclosure also contemplates the use of structures to set and/or adjust an amount of compression of actuation element guides so as to achieve the desired pre-compression. Turning to FIG. 11, an exemplary embodiment of a proximal portion 1100 of a surgical instrument is shown, which includes a shaft 1120 and a force transmission mechanism 1110. Shaft 1120 and force transmission mechanism 1110 may be configured according to the exemplary embodiments of FIGS. 1-10. For example, force transmission mechanism 1110 may include actuation input mechanisms 1130 to actuate actuation elements 1132, which are connected to actuation input mechanisms 1130 and extend through shaft 1120. Actuation input mechanisms 1130 may be capstans and actuation elements 1132 may be, for example, cables, although the exemplary embodiments described herein are not limited to this configuration. Force transmission mechanism 1110 may further include an actuation input mechanism 1124 to engage a roll gear 1122 and roll shaft 1120

Structures to Set and/or Adjust Compression of Actuation Element Guides

As depicted in the exemplary embodiment of FIG. 11, force transmission mechanism 1110 includes a block 1140 held in a mount 1142. Block 1140 may be configured, for example, according to block 430 in the exemplary embodiment of FIG. 4. For example, an array of actuation element guides 1150, which may be configured according to the exemplary embodiments of FIGS. 4-10, is held by block 1140 and a block (not shown, such as block 432 in FIG. 4) at a distal portion of shaft 1120. Block 1140 may be held in mount 1142 so that an amount of compression exerted upon actuation element guides 1150 can be set and/or adjusted. Setting and/or adjusting an amount of compression of an actuation element guide can be accomplished during the assembly and/or reprocessing of an instrument. For example, an amount of compression of an actuation element guide may be set and/or adjusted during assembly of an instrument, for example to compensate for length differences due to variation in manufacturing processes. The amount of compression of an actuation element guide may be reset and/or readjusted during reprocessing of the instrument for further use.

Figure 12:
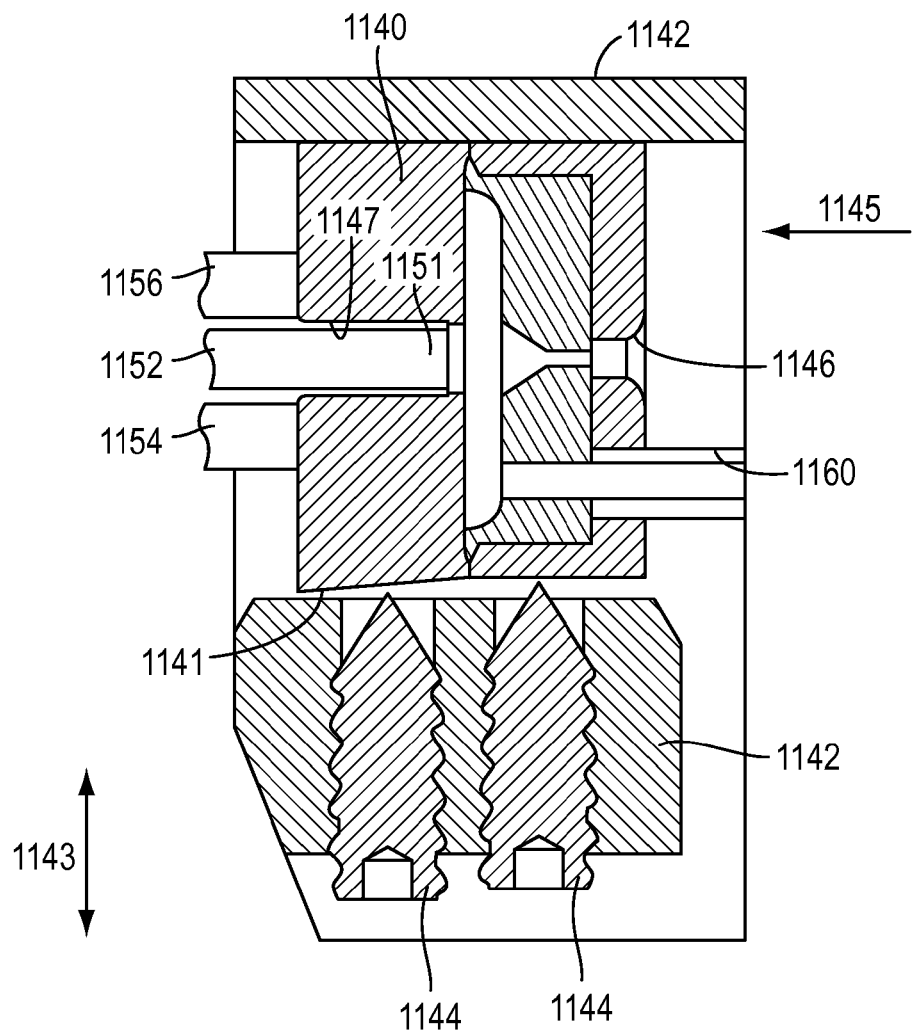
FIG. 12 is a cross-sectional view of a mount and block for actuation element guides, according to an exemplary embodiment.

As shown in the exemplary embodiment of FIG. 12, mount 1142 includes one or more set screws 1144 that engage a surface 1141 of block 1140. The compression of actuation element guides 1152, 1154, 1156 held within block 1140 is set by applying a force to block 1140 to compress actuation element guides 1152, 1154, 1156, such as by applying a force to block 1140 along direction 1145 in the exemplary embodiment of FIG. 12, and adjusting set screws 1144 along the directions indicated by arrows 1143 in FIG. 12 until the set screws 1144 engage surface 1141 of block 1140 to maintain block 1140 in its position and maintain actuation element guides 1152, 1154, 1156 in a compressed state. According to an exemplary embodiment, surface 1141 may be sloped to facilitate maintaining block 1140 in its set position, such as when block 1140 is subjected to loads during use of a surgical instrument including block 1140, such as from actuation elements (not shown in FIG. 12) extending through actuation element guides 1152, 1154, 1156 and block 1140.

Actuation element guides 1152, 1154, 1156 may be held by block 1140 within individual holes, such as by disposing a proximal end 1151 of actuation element guide 1152 within hole 1147 of block 1140. Block 1140 also includes individual passages, such as passage 1146, to receive actuation elements (e.g. actuation elements 1132 in FIG. 11) and route the actuation elements to individual actuation element guides 1152, 1154, 1156. Although only three actuation element guides 1152, 1154, 1156 are depicted in the exemplary embodiment of FIG. 12, other numbers of actuation element guides and a corresponding number of actuation elements may be utilized, such as, for example, one, two, four, five, seven, eight, nine, ten, or more.

Other structures may be utilized to set and/or adjust an amount of compression to achieve the pre-compression of actuation element guides. As depicted in the exemplary embodiment of FIG. 13, an actuation element guide 1250 extends from an instrument shaft 1220 to a block 1240 located within a force transmission mechanism of an instrument. Actuation element guide 1250, shaft 1220, and a proximal block 1240 may be arranged according to the exemplary embodiments of FIGS. 4-10. As depicted in the exemplary embodiment of FIG. 13, block 1240 includes one or more passages 1244 through which one or more actuation element(s) (not shown) respectively extend to one or more actuation element guide(s) 1250. Block 1240 may be held by a mount 1242, as illustrated in FIG. 13.

Figure 13:
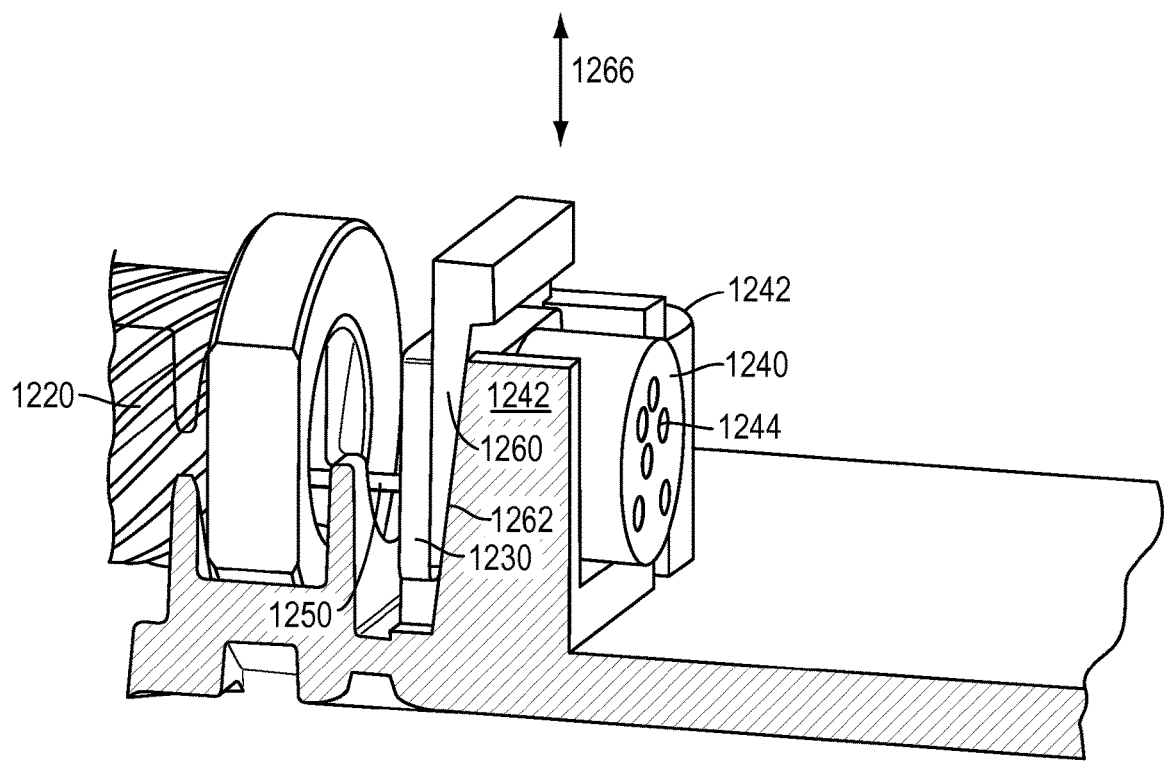
FIG. 13 is a side perspective view of a structure to set and/or adjust the compression of actuation element guides, according to an exemplary embodiment.

A wedge 1260 inserted between a plate 1230 and block 1240, such as along the directions indicated by arrows 1266 in FIG. 13, can be used to set and/or adjust an amount of compression exerted by block 1240 upon actuation element guide 1250. Wedge 1260 has an inclined surface 1262 that is urged against block 1240 as the wedge 1260 is inserted between plate 1230 and block 1240. Because surface 1262 is a continuous linear surface, wedge 1260 provides a linear, continuously variable ability to adjust and/or set the amount of compression for actuation element guide 1250 via moving block 1240 as the position of wedge 1260 is adjusted between plate 1230 and block 1240. Surface 1262 may have an incline ranging from about 5 to about 10 degrees, according to an exemplary embodiment. According to an exemplary embodiment, a hold-down member (not shown) is provided to contact a top surface of wedge 1260 and facilitate maintaining a position of wedge 1260 between plate 1230 and block 1240. Suitable hold down members include, but are not limited to, a fastener (e.g., set screw), flexure member, adhesive, weld, deformed member, or other structures familiar to one of ordinary skill in the art.

Figure 14:
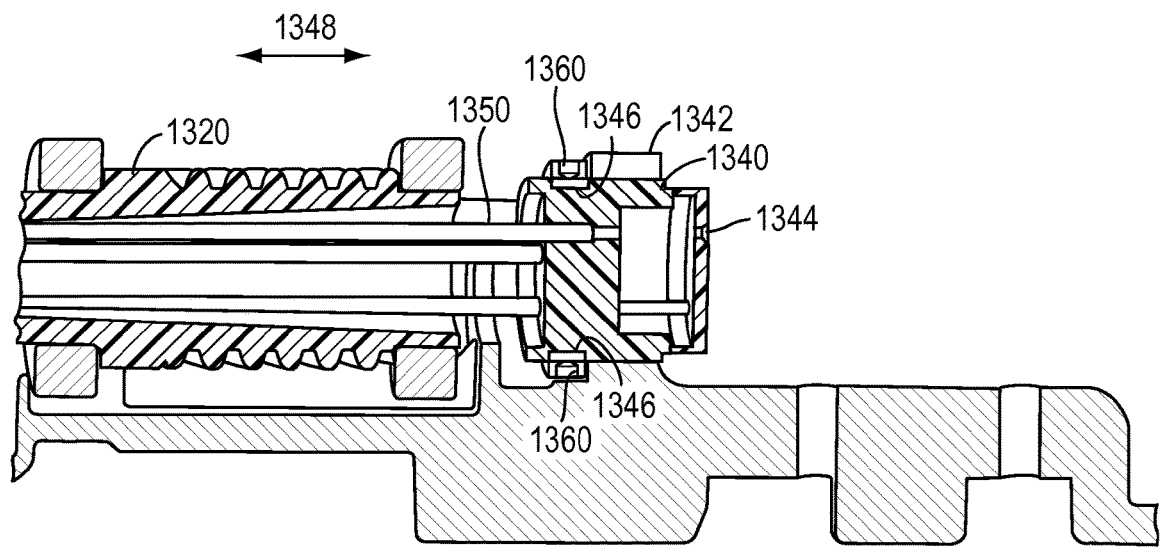
FIG. 14 is a side view of a structure to set and/or adjust the compression of actuation element guides, according to another exemplary embodiment.

Another exemplary embodiment for setting and/or adjusting an amount of compression of actuation element guides is depicted in FIG. 14. As shown in FIG. 14, one or more actuation element guide(s) 1350 may extend through a shaft 1320 of an instrument to a block 1340 located within a force transmission mechanism of the instrument. Actuation element guide 1350, shaft 1320, and block 1340 may be arranged according to the exemplary embodiments of FIGS. 4-10. Block 1340 may be held within a mount 1342, as shown in FIG. 14, and may include one or more passage(s) for actuation element(s) (not shown) to extend through block 1340 to respective one or more actuation element guide(s) 1350. Block 1340 includes screw threads 1346 that engage with a threaded nut 1360. As depicted in the exemplary embodiment of FIG. 14, nut 1360 engages with mount 1342 so that the position of nut 1360 is fixed along the directions indicated by arrows 1348 in FIG. 14. As a result, when nut 1360 is rotated relative to block 1340 (e.g., to tighten or loosen nut 1360), mount 1340 is moved along the directions indicated by arrows 1348, which sets and/or adjusts the compression exerted by block 1340 upon the one or more actuation element guide(s) 1350.

Figure 15:
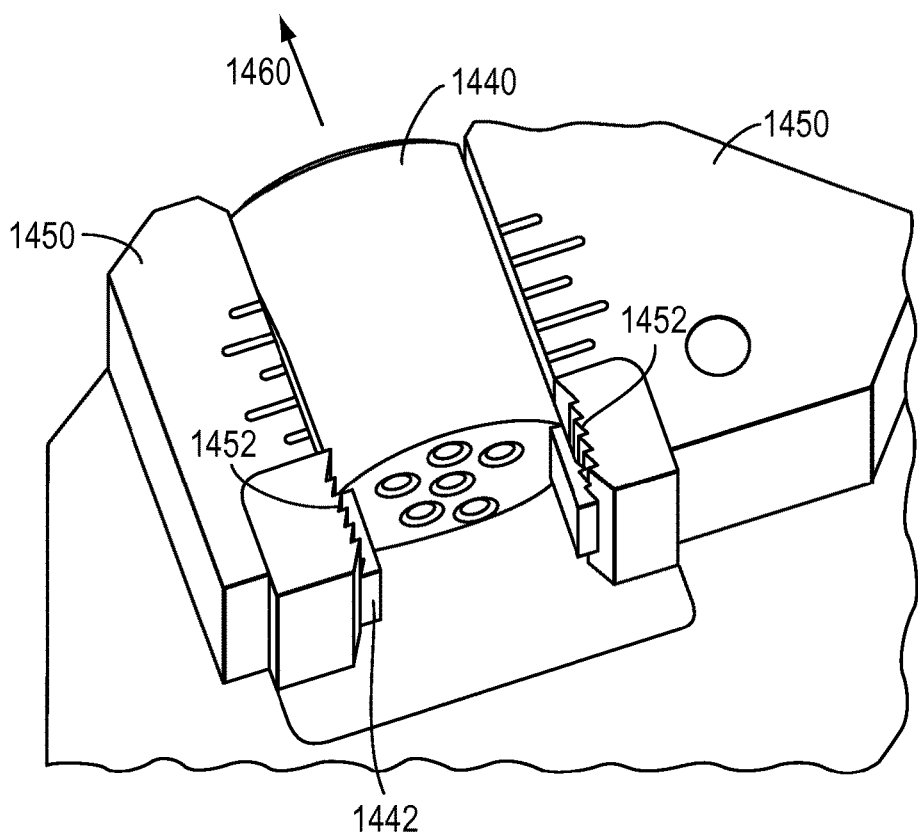
FIG. 15 is a perspective view of a structure to set and/or adjust the compression of actuation element guides, according to another exemplary embodiment.

FIG. 15 depicts yet another exemplary embodiment for setting and/or adjusting an amount of compression of actuation element guides, which includes a block 1440 disposed in a force transmission mechanism of an instrument and held by a mount 1450. Block 1440 may be made of, for example, a metal, such as a stainless steel alloy, or a polymer (e.g., an injected molded polymer), according to an exemplary embodiment. Mount 1450 may be fixed to a force transmission mechanism (e.g., force transmission mechanism 1110 of the exemplary embodiment of FIG. 11) or mount 1450 may be integrally formed as a part of a chassis of a force transmission mechanism, according to an exemplary embodiment.

Block 1440 may be arranged according to the exemplary embodiments of FIGS. 4-10, except that block 1440 includes one or more ratchet teeth 1442, as depicted in the exemplary embodiment of FIG. 15. Mount 1450 in turn includes one or more ratchet pawls 1452 that engage the ratchet teeth 1442, according to an exemplary embodiment. For example, block 1440 may be moved along the direction indicated by arrow 1460 in FIG. 15 to increase the amount of compression applied by block 1440 to one or more actuation element guide(s) (not shown). As block 1440 is moved, ratchet teeth 1442 slide past ratchet pawl 1452 so that the amount of compression applied by block 1440 may be set and/or adjusted. Ratchet teeth 1442 may flex and move toward one another to facilitate movement of ratchet projections 1442 over ratchet portions 1452 as block 1440 is moved along direction 1460, according to an exemplary embodiment. According to an exemplary embodiment, the distance between consecutive ratchet teeth 1442 along direction 1460 may be varied to provide a desired control for varying the amount of compression applied by block 1440.

Figure 16:
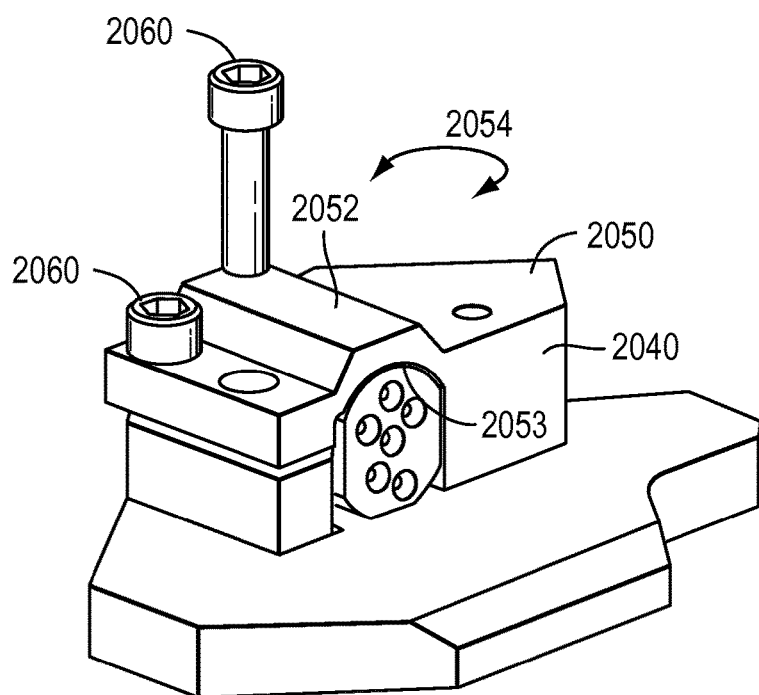
FIG. 16 is a perspective view of a block and mount to set and/or adjust the compression of actuation element guides, according to an exemplary embodiment.

FIG. 16 depicts another exemplary embodiment for setting and/or adjusting an amount of compression of actuation element guides, which includes a block 2040 disposed in a force transmission mechanism of an instrument and held by a mount 2050. Block 2040 may be arranged according to the exemplary embodiments of FIGS. 4-10. According to an exemplary embodiment, mount 2050 includes a clamp portion 2052 that applies pressure to an outer diameter of block 2040 to set the compression applied by block 2040 to one or more actuation element guide(s) (not shown), such as by fastening clamp portion 2052 to mount 2050 (e.g., via one or more screws 2060). Clamp portion 2052 can be manufactured as an integral, single piece with mount 2050, with clamp portion 2052 having a thickness to facilitate elastic deformation of clamp portion 2052. For example, clamp portion 2052 may be pivotably mounted relative to mount 2050, such as along directions 2054 in the exemplary embodiment of FIG. 16. Clamp portion 2052 includes a surface 2053 having a shape complementary to a shape of block 2040. Mount 2050 and clamp portion 2052 can be made of, for example, machined metal (e.g., a stainless steel alloy), a polymer material (e.g., an injection molded polymer material), or other material familiar to one of ordinary skill in the art. According to another exemplary embodiment, clamp portion 2052 is provided as a separate piece that is fastened to mount 2050, such as via screws.

Figure 17:
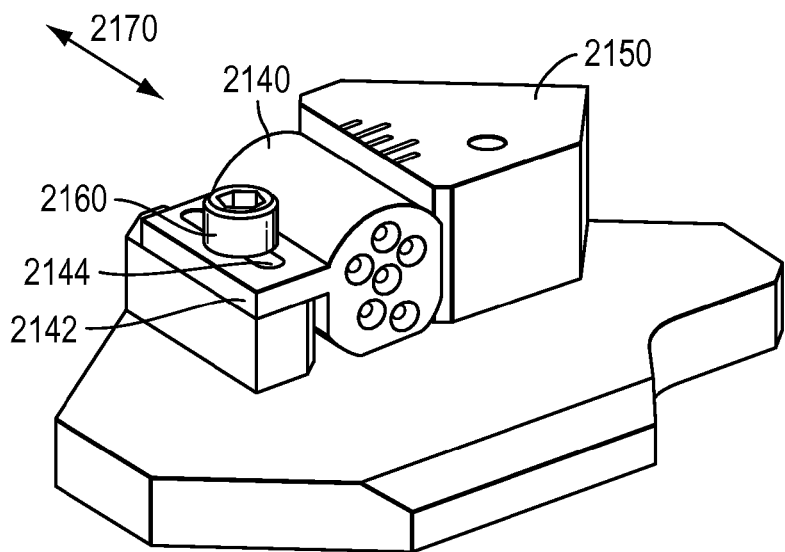
FIG. 17 is a perspective view of a block and mount to set and/or adjust the compression of actuation element guides, according to another exemplary embodiment.

Other clamping configurations are contemplated by the various exemplary embodiments described herein for setting and/or adjusting an amount of compression of actuation element guides. FIG. 17 depicts another exemplary embodiment that includes a block 2140 disposed in a force transmission mechanism of an instrument and held by a mount 2150. Block 2140 may be arranged according to the exemplary embodiments of FIGS. 4-10 except that block 2140 includes a flange portion 2142 to be fastened to mount 2150, such as via one or more screws 2160. Flange portion 2142 includes an elongated aperture 2144, as depicted in the exemplary embodiment of FIG. 17. Elongated aperture 2144 is larger than screw 2160, permitting the position of block 2170 to be adjusted along directions 2170, while also permitting block 2170 to be fastened to mount 2150 via screw 2160, so that an amount of compression of actuation element guides (not shown) mounted to block 2140 may be set and/or adjusted.

In another exemplary embodiment for setting and/or adjusting an amount of compression of actuation element guides, a block may include a plurality of concentric tapered fittings that may be adjusted along an axial length of the block and fixed to one another to set and/or adjust the compression applied by the block. Other structures for setting and/or adjusting the compression applied by the block to one or more actuation element guide(s) that may be familiar to one of ordinary skill in the art are contemplated as within the scope of the present disclosure.

Reprocessing of Instruments Including Actuation Element Guides

Figure 18:
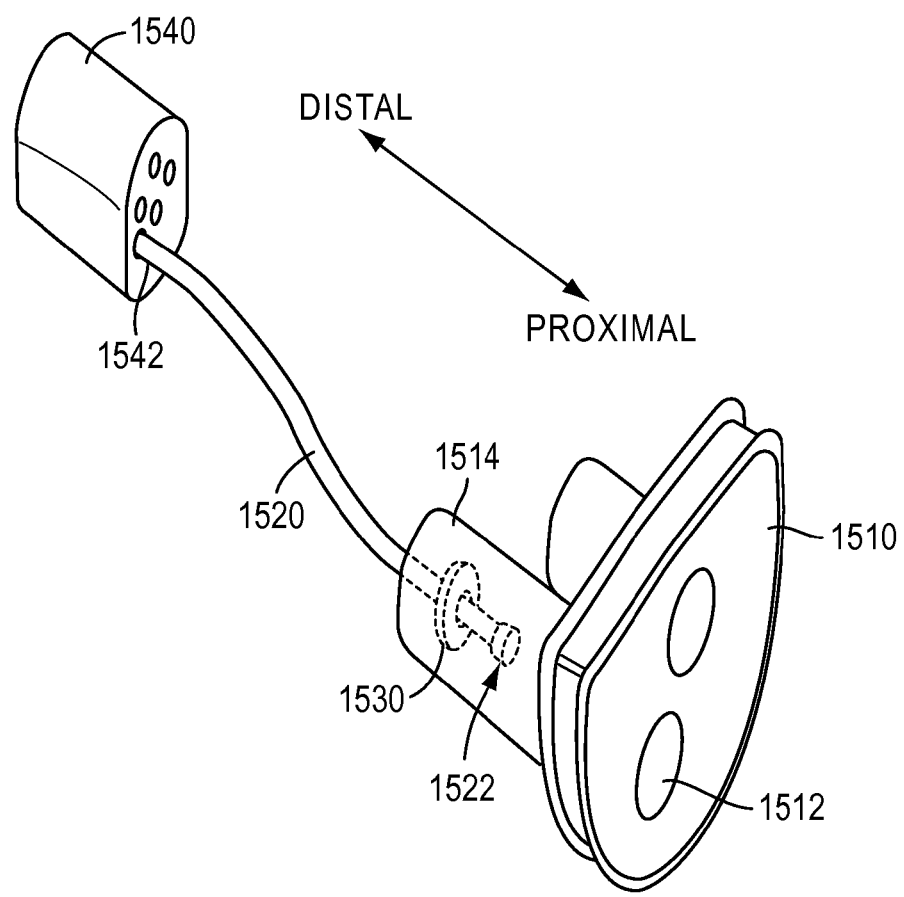
FIG. 18 is a perspective view of a block, flush tube, and flush plate for a surgical instrument, according to another exemplary embodiment.

A surgical instrument also may include structures to facilitate cleaning of the surgical instrument, such as a flush tube 1160 depicted in FIGS. 11 and 12. Turning to FIG. 18, a block 1540, flush tube 1520, and flush plate 1510 are depicted. These components may be located within a force transmission mechanism (not shown) of a surgical instrument. Block 1540 may be configured according to the exemplary embodiments of FIGS. 4 and 11-15. Flush plate 1510 may form an outer surface of a force transmission mechanism so that a fluid source (e.g., a cleaning fluid source) connected to flush plate 1510 can deliver fluid into the surgical instrument during a cleaning procedure. For example, flush plate 1510 may include a flush port 1512 fluidically connected to flush tube 1520, which is in turn fluidically connected to block 1542. As shown in the exemplary embodiment of FIG. 18, a first end 1522 of flush tube 1522 is located within a channel 1514 fluidically connected to flush port 1512, with channel 1514 being sealed with flush tube 1520. For instance, a seal 1530 may be disposed within channel 1514 to seal flush tube 1520 with channel 1514. Flush tube 1520 may be disposed within an aperture 1542 of block 1540 to connect flush tube 1520 to block 1540, as shown in the exemplary embodiment of FIG. 18. Flush tube 1520 may be sealed to block 1540, such as via, for example, welding flush tube 1520 to block 1540.

Figure 19:
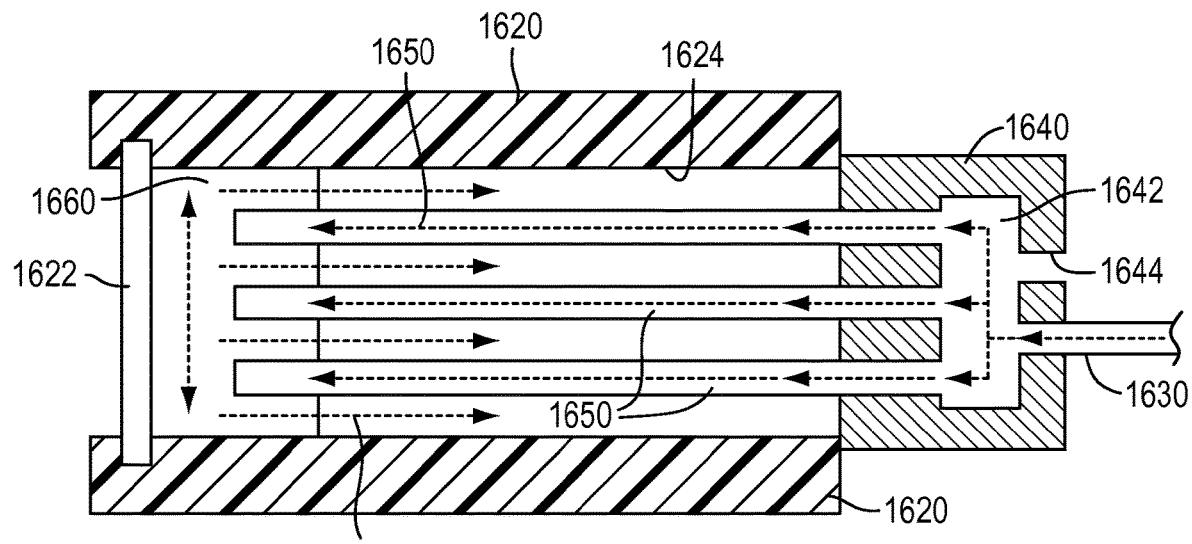
FIG. 19 is a cross-sectional view of cleaning passages within a shaft of a surgical instrument, according to another exemplary embodiment.

Fluid delivered to a block, such as via a flush tube, may be distributed among various actuation element guides coupled to the block so the fluid may flow through the guides during a cleaning procedure. As schematically depicted in FIG. 19, a plurality of actuation element guides 1650 are coupled to a block 1640, which may be fluidically connected to a flush tube 1630, as described above with regard to the exemplary embodiment of FIG. 18, and include one or more passage(s) 1644 through which one or more actuation element(s) (not shown) may extend to the actuation element guides 1650. According to an exemplary embodiment, proximal block 1640 includes a distribution chamber 1642 through which fluid supplied from flush tube 1630 may be distributed to the various actuation element guides 1650. As schematically depicted in the exemplary embodiment of FIG. 19, fluid flows through an interior of actuation element guides 1650 that are disposed within an instrument shaft 1620 until the fluid reaches the distal ends of the guides 1650, which are coupled to a distal block 1660, as discussed above with regard to the exemplary embodiment of FIG. 4. Fluid exits the actuation element guides 1650 and distal block 1660 and, due to a shaft seal 1622, is directed through an interior of shaft 1620 between an inner wall 1624 of shaft 1620 and guides 1650. For example, shaft 1620 may include an open space 1624 between inner wall 1624 and guides 1650, as discussed above with regard to the exemplary embodiment of FIG. 4, and fluid exiting the guides 1650 is directed through open space 1624 back towards block 1640 to facilitate cleaning an interior of shaft and the exterior of guides 1650. According to an exemplary embodiment, the fluid exits shaft 1620, such as via one or more aperture(s) (not shown) in shaft 1620 proximate to block 1640.

Figure 20:
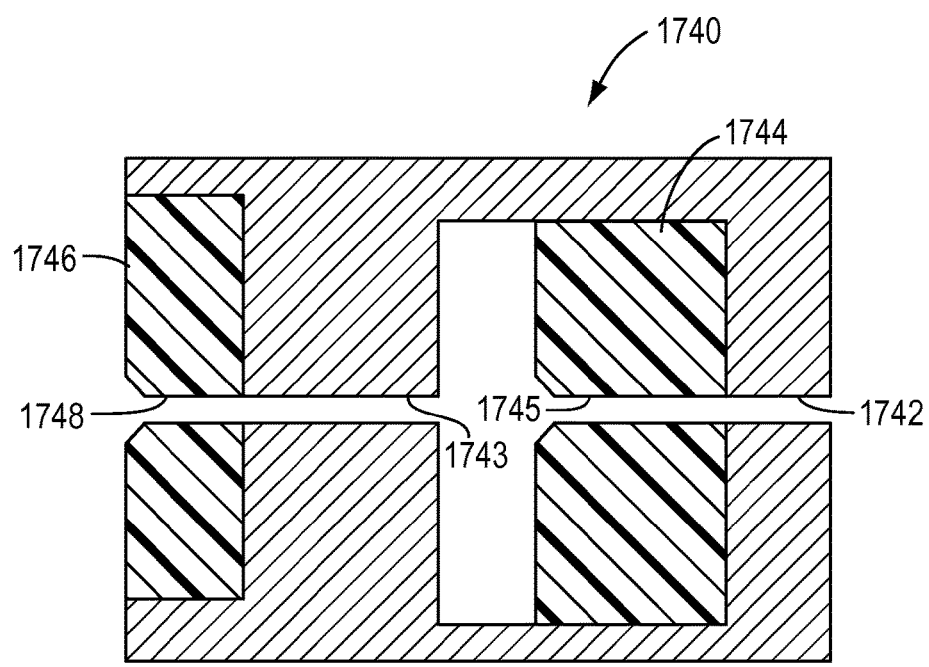
FIG. 20 is a cross-sectional view of a compression block including seals, according to another exemplary embodiment.

Blocks of the various exemplary embodiments described herein may include sealing structures to facilitate forming a seal between the block and the various actuation elements and actuation element guides connected to a block. Turning to FIG. 20, a block 1740 is depicted that includes a first passage 1742 to receive an actuation element (not shown) and a second passage 1743 to direct the actuation element into an actuation element guide (not shown) connected to second passage 1743. To seal block 1740 to the actuation element and the guide, block 1740 may include a first seal 1744 including a channel 1745 and a second seal 1746 including a channel 1748. Although a single passage and channel is depicted through each of block 1740 and seals 1744, 1746, each of block 1740 and seals 1744, 1746 may include a plurality of passages and channels corresponding to a number of actuation elements of an instrument, such as, for example, two, three, four, five, six, seven, or eight or more. Seals 1744, 1746 may be made of, for example, an elastomer, such as rubber, or other seal material familiar to one of ordinary skill in the art. According to an exemplary embodiment, passages 1745, 1748 may have a diameter equal to or less than a diameter of an actuation element extending through passages 1745, 1748 to facilitate sealing with the actuation element. According to an exemplary embodiment, block 1740 may be disposed within a force transmission mechanism of a surgical instrument and may include other features, such as the features of the various exemplary embodiments of FIGS. 4-17 described above.

Blocks 1140, 1240, 1340, 1440, 1540, 1640, 1740, 2040, 2140 of the exemplary embodiments of FIGS. 11-20 may be stationary, with actuation element guides compressed by blocks 1140, 1240, 1340, 1440, 1540, 1640, 1740, 2040, 2140 and also rotatable relative to blocks 1140, 1240, 1340, 1440, 1540, 1640, 1740, 2040, 2140 such as when a shaft through which the actuation element guides extend is rotated. The blocks may further contain a manifold to distribute cleaning fluid to various actuation element guides compressed by the blocks, such as according to the exemplary embodiment of FIG. 19. Thus, blocks 1140, 1240, 1340, 1440, 1540, 1640, 1740 can provide a dual function of both compressing actuation element guides and routing cleaning fluid to various actuation element guides, such as from a single inlet in the block.

Figure 21:
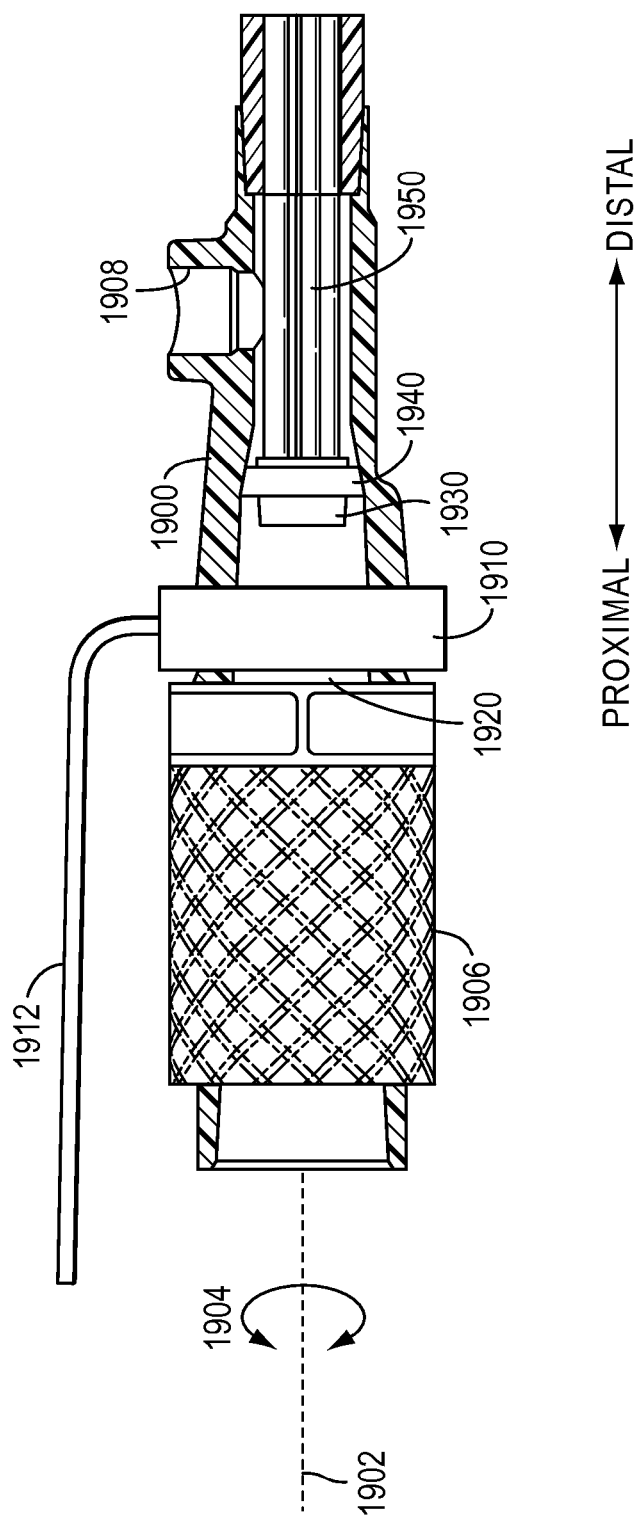
FIG. 21 is a side partial sectional view of a proximal portion of an instrument shaft, according to an exemplary embodiment.
Figure 22:
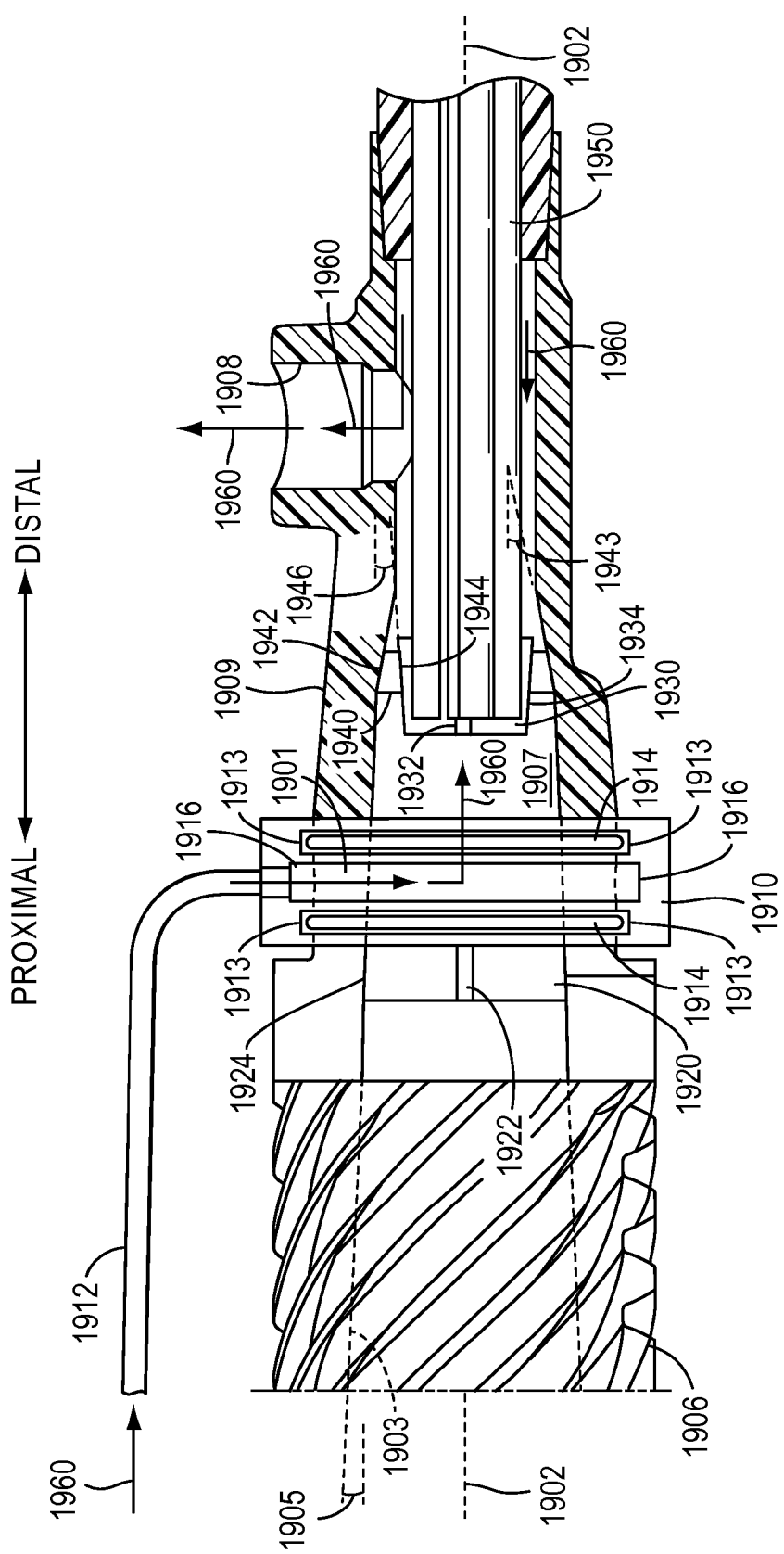
FIG. 22 is a side sectional view of the instrument shaft portion of FIG. 21.

Structures to Set and/or Adjust Compression of Actuation Element Guides with Instrument Shaft The various exemplary embodiments described herein contemplate other structures for blocks to compress actuation element guides. Turning to FIG. 21, an exemplary embodiment of a proximal portion 1900 of an instrument shaft is depicted. As depicted in the exemplary embodiment of FIG. 21, instrument shaft portion 1900 includes a roll gear 1906 so that instrument shaft portion 1900 may be rotated about its longitudinal axis 1902, such as along the directions indicated by arrows 1904 in FIG. 21. Instrument shaft portion 1900 includes a proximal block 1930 to compress one or more actuation element guides 1950, such as according to the exemplary embodiments of FIGS. 4-6, 9, and 10. As depicted in FIG. 22, proximal block 1930 may include one or more passages 1932 corresponding to the number of actuation elements (not shown) extending through proximal block 1930 and through the one or more actuation element guides 1950.

To compress the one or more actuation element guides 1950, proximal block 1930 may be fixed to an interior surface 1903 of instrument shaft portion 1900. For example, proximal block 1930 is connected to a fitting 1940 that is fixed to instrument shaft portion 1900. Fitting 1940 is fixed to instrument shaft portion 1900 by welding fitting 1940 to instrument shaft portion 1900, according to an exemplary embodiment. For example, fitting 1940 can be welded to instrument shaft portion 1900 by irradiating outer radial surface 1909 of instrument shaft portion 1900, which may be made of a transparent or translucent material, such as, for example, PEEK or another polymer that is transparent or translucent, with a laser so the laser passes through instrument shaft portion 1900 and impinges upon fitting 1940. In such an embodiment, fitting 1940 is made of a material that is heated by the laser, such as, for example, PEEK or another polymer having an opaque color, according to an exemplary embodiment. However, other methods may be used to fix fitting 1940 to instrument shaft portion 1900, such as by using fasteners, a friction fit construction, and other methods familiar to one of ordinary skill in the art.

According to an exemplary embodiment, proximal block 1930 has a friction fit connection with fitting 1940. As shown in the exemplary embodiment of FIG. 22, proximal block 1930 has a sloped outer radial surface 1934 with respect to instrument axis 1902 and fitting 1940 has a sloped inner radial surface 1944. According to an exemplary embodiment, the slope of outer radial surface 1934 of proximal block 1930 forms an angle 1946 ranging, for example, from about 5 degrees to about 25 degrees with respect to instrument axis 1902. According to an exemplary embodiment, the slope of inner radial surface 1944 of fitting 1940 forms an angle 1946 ranging, for example, from about 2 degrees to about 10 degrees with respect to instrument axis 1902. According to an exemplary embodiment, proximal block 1930 is inserted within central aperture 1948 of fitting 1940 (shown in FIG. 23) to fix proximal block 1930 to instrument shaft portion 1900, such as via the connection between fitting 1940 and instrument shaft portion 1900. At least one of proximal block 1930 and fitting 1940 may include a split along axis 1902 to facilitate changes in the diameter of proximal block 1930 and/or fitting 1940 as fitting 1940 and proximal block 1930 are placed in set positions within the instrument shaft.

Proximal block 1930 and the one or more actuation element guides 1950 can be sealed to one another to facilitate flushing of cleaning fluid through the one or more actuation element guides 1950 so that cleaning fluid entering proximal block 1930 via passages 1932 is directed into an interior of actuation element guides 1950. For example, proximal block 1930 is made of a metal, such as a stainless steel or a plastic, with the metal or plastic material of proximal block 1930 sealing to the one or more actuation element guides 1950. In another example, proximal block 1930 includes one or more seals (not shown), such as, for example, an elastomer seal, that seals with the one or more actuation element guides 1950, as discussed above with regard to the exemplary embodiment of FIG. 22. According to an exemplary embodiment, passages 1932 may be dimensioned to permit both actuation elements and cleaning fluid to enter proximal block 1930 via passages 1932.

According to an exemplary embodiment, one or more actuation element guides 1950 are mounted within proximal block 1930 to compress the one or more actuation element guides 1950 between proximal block 1930 and a distal block (not shown), as discussed above with regard to the exemplary embodiment of FIGS. 4-6, 9, and 10. Thus, an amount of compression of the one or more actuation element guides 1950 may be set and/or adjusted, such as during assembly of an instrument and/or during reprocessing of an instrument. To provide a predetermined amount of compression to the one or more actuation element guides 1950, outer radial surface 1942 of fitting 1940 and at least a portion of interior surface 1903 of instrument shaft portion 1900 are sloped a desired amount, according to an exemplary embodiment. For example, each outer radial surface 1942 and interior surface 1903 (e.g., a portion of interior surface 1903 where fitting 1940 is installed) have an angle 1943 ranging from, for example, about 2 to about 10 with respect to instrument axis 1902. According to an exemplary embodiment, a method of manufacturing an instrument may include mounting one or more actuation element guides 1950 within proximal block 1930 within instrument shaft portion 1900 and installing fitting 1940 between proximal block 1930 and interior surface 1903 of instrument shaft portion 1900 so that fitting 1940 is wedged between proximal block 1930 and surface 1903. Subsequently, fitting 1940 is fixed to surface 1903 to maintain a predetermined amount of compression of the at least one actuation element guide 1950.

Reprocessing of Instrument with Shafts that Engage with Structures to Set and/or Adjust Compression of Actuation Element Guides According to an exemplary embodiment, instrument shaft portion 1900 is configured to receive cleaning fluid to facilitate reprocessing of an instrument including instrument shaft portion 1900. As depicted in the exemplary embodiment of FIGS. 21-23, a bushing 1910 is connected to instrument shaft portion 1900 to supply cleaning fluid to instrument shaft portion 1900. For instance, a tube 1912 may be connected to bushing 1910 and to a flush port (not shown) to receive cleaning fluid, as discussed above.

Due to the connection between fitting 1940 and instrument shaft portion 1900, as well as between the connection between proximal block 1930 and fitting 1940, the one or more actuation element guides 1950, proximal block 1930, and fitting 1940 rotate with instrument shaft portion 1900 about axis 1902, such as when a rolling input is made to roll gear 1906. Because tube 1912 is connected to a flush port, such as a flush port located in a force transmission mechanism (not shown) of an instrument including instrument shaft portion 1900, tube 1912 and bushing 1910 do not rotate with instrument shaft portion 1900 about axis 1901. Therefore, bushing 1910 is configured to provide a rotary seal between bushing 1910 and instrument shaft portion 1900 to permit instrument shaft portion 1900 to rotate relative to bushing 1910 and tube 1912, while permitting cleaning fluid 1960 to be supplied through tube 1912 and bushing 1910 to instrument shaft portion 1900. Further, by providing a cleaning fluid connection between tube 1912 and instrument shaft portion 1900 via bushing 1910 instead of proximal block 1930, proximal block 1930 may utilize a simple construction that does not include manifold passages to route the cleaning fluid from a single fluid inlet to various actuation element guides 1950 extending through proximal block 1930. According to an exemplary embodiment, tube 1912 and bushing 1910 may be made of, for example, a polymer or a metal, such as a stainless steel or another alloy familiar to one of ordinary skill in the art.

Figure 23:
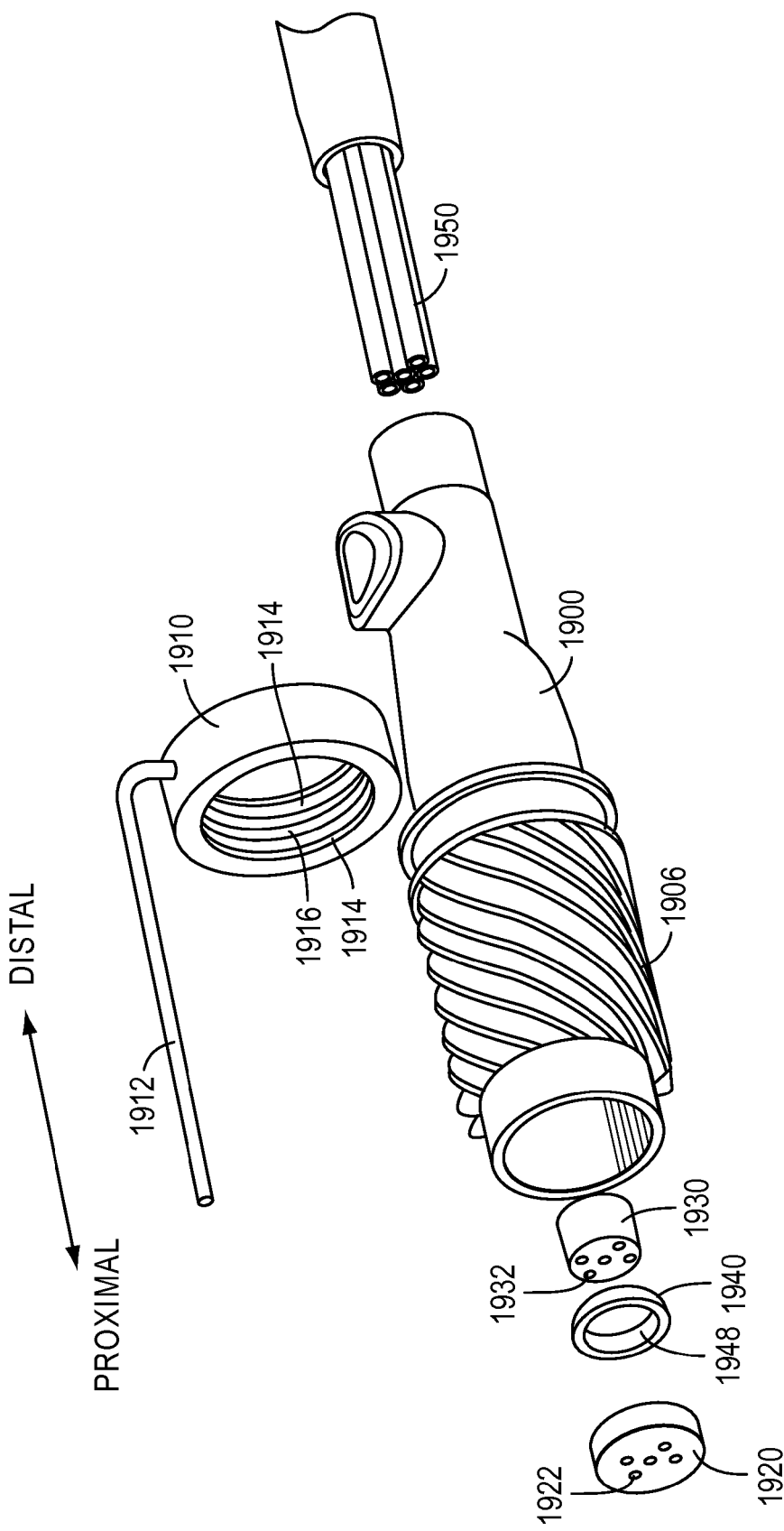
FIG. 23 is an exploded view of the instrument shaft portion of FIG. 21.

Bushing 1910 also may include one or more seals 1914 (e.g., elastomer seals) respectively mounted within grooves 1913 of bushing 1910 to form a seal between bushing 1910 and an outer radial surface 1909 of instrument shaft portion 1900. Seals 1914 are configured to fluidically seal against outer radial surface 1909, even as instrument shaft portion 1900 rotates relative to bushing 1910. As shown in FIGS. 22 and 23, bushing 1910 may include an annular manifold 1916 located between seals 1914, along an axial direction (e.g., proximal-distal direction) of instrument shaft portion 1900. Annular manifold 1916 may surround instrument shaft portion 1900 so that cleaning fluid 1960 supplied to manifold 1916 via tube 1912 flows about an outer surface of instrument shaft portion 1900 until the cleaning fluid 1960 reaches a fluid inlet 1901 and flows into an interior chamber 1907 within instrument shaft portion 1900, as depicted in FIG. 22.

Instrument shaft portion 1900 includes a seal block 1920 to direct cleaning fluid 1960 into the one or more passages 1932 of proximal block 1930 and respective actuation element guides 1950. Seal block 1920 includes one or more passages 1922 corresponding to the number of actuation elements (not shown) extending through seal block 1920 and proximal block 1930. Seal block 1920 seals with the actuation elements. According to an exemplary embodiment, seal block 1920 is made of a metal, such as stainless steel, that contacts and seals with the actuation elements extending through seal block 1920. According to another exemplary embodiment, seal block 1920 includes seals (e.g., elastomer seals) that engage and seal with the actuation elements, similar to the exemplary embodiment of FIG. 22. To hold seal block 1920 in position, seal block 1920 can be fixed to inner surface 1903 of instrument shaft portion 1900. For example, surface 1924 of seal block 1920 and inner surface 1903 of instrument shaft portion 1900 are sloped at an angle 1905 ranging, for example, from about 1 degree to about 7 degrees with respect to instrument axis 1902 to provide a friction fit between seal block 1920 and instrument shaft portion 1900.

Due to the sealed arrangement between seal block 1920 and instrument shaft portion 1900, between fitting 1940 and instrument shaft portion 1900, and between proximal block 1930 and fitting 1940, cleaning fluid entering chamber 1907 from bushing 1910 is forced through the one or more passages 1932 of proximal block 1930 and into the one or more actuation element guides 1950 compressed by proximal block 1930. As a result, the cleaning fluid 1960 flows through an interior of the one or more actuation element guides 1950 along an axial direction of the instrument until the cleaning fluid reaches a distal block (not shown), where the cleaning fluid 1960 exits the one or more actuation element guides 1950 and flows around an exterior of the one or more actuation element guides 1950 to reprocess an interior of instrument shaft portion 1900 before exiting instrument shaft portion 1900, such as via flush exit port 1908.

Figure 24:
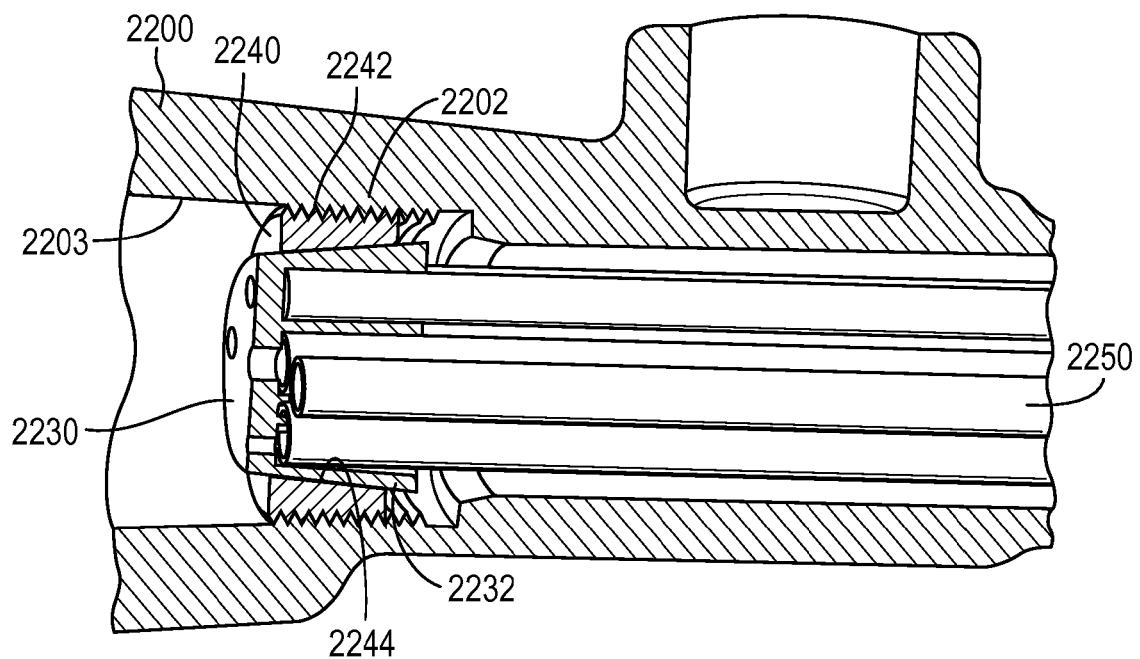
FIG. 24 is a side partial sectional view of a proximal portion of an instrument shaft, according to another exemplary embodiment.

Additional Structures to Set and/or Adjust Compression of Actuation Element Guides with Instrument Shaft Other instrument arrangements are contemplated by the various exemplary embodiments described herein. Turning to FIG. 24, an exemplary embodiment of a proximal portion 2200 of an instrument shaft is depicted. According to an exemplary embodiment, proximal portion 2200 of instrument shaft includes a proximal block 2230 one or more actuation element guides 2250 are mounted to and a fitting 2240 that proximal block 2230 engages with, as described above with regard to FIGS. 21-23. According to an exemplary embodiment, proximal block 2240 includes a sloped outer radial surface 2232 and fitting 2240 includes a sloped inner radial surface 2244, as discussed above with regard to the exemplary embodiment of FIGS. 21-23. Fitting 2240 is fixed to shaft 2200, as discussed above with regard to the exemplary embodiment of FIGS. 21-23, except that fitting 2240 includes a threaded portion 2242 and an inner radial surface 2203 of shaft portion 1900 includes a corresponding threaded portion 2202 to facilitate setting and/or adjusting a predetermined amount of compression to the one or more actuation element guides 2250, according to an exemplary embodiment. For example, the position of fitting 2240 and proximal block 2230 moved along directions 2260 in the exemplary embodiment of FIG. 24 by screwing fitting 2240 along threaded portion 2202 to set and/or adjust a predetermined amount of compression to the one or more actuation element guides 2250.

Figure 25:
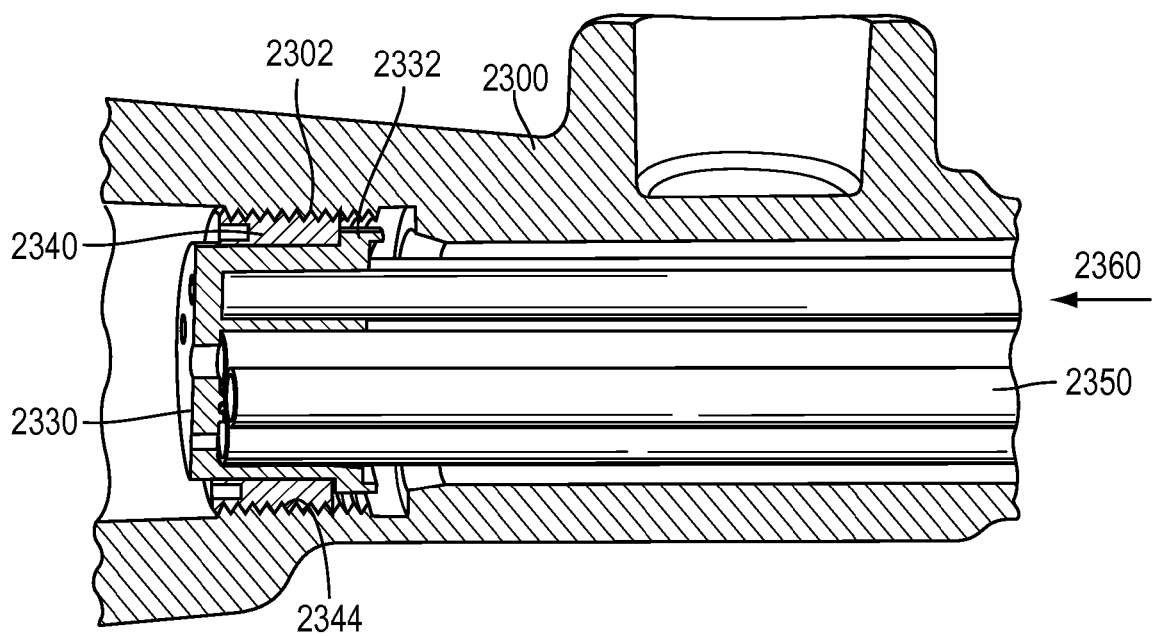
FIG. 25 is a side partial sectional view of a proximal portion of an instrument shaft, according to another exemplary embodiment.

FIG. 25 depicts an exemplary embodiment of a proximal portion 2300 of an instrument shaft that includes a proximal block 2330, a fitting 2340, and one or more actuation element guides 2350 mounted to proximal block 2330. Shaft portion 2300 and fitting 2340 respectfully include threaded portions 2302, 2344, as discussed above with regard to the exemplary embodiment of FIG. 24, to facilitate setting and/or adjusting an amount of compression of the one or more actuation element guides 2350. Proximal block 2330 and fitting 2340 differ by not including sloped radial surfaces. Instead, proximal block 2330 includes a flange 2332 to engage with fitting 2340, according to an exemplary embodiment. As a result, when the one or more actuation element guides 2350 apply a force to proximal block 2330 along direction 2360 in the exemplary embodiment of FIG. 25, proximal block 2330 is forced against fitting 2340 to maintain a position of proximal block 2330 relative to fitting 2340.

Although the various exemplary embodiments described herein contemplate including the various cleaning structures described herein, a surgical instrument may lack the cleaning structures described. For example, a surgical instrument may be a single-use surgical instrument and therefore lack structures to facilitate cleaning of the instrument.

Actuation Element Guides Including Portions with Different Amounts of Twist

Figure 26:
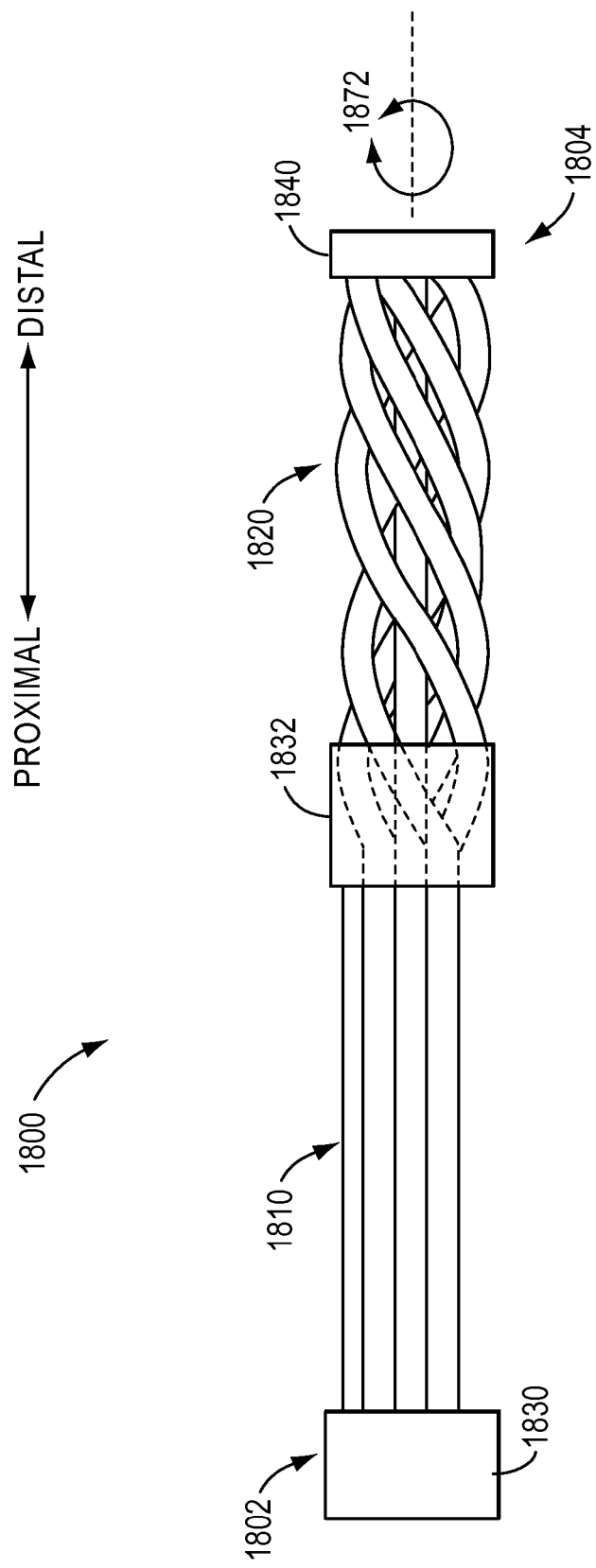
FIG. 26 is a side view of an actuation element guide bundle, according to another exemplary embodiment.

Other structures are contemplated by the various exemplary embodiments described herein. For example, the proximal block 430 of FIG. 4 has been described as being located at a proximal portion 412 of shaft 400, such as by being disposed within a force transmission mechanism of an instrument. As a result, actuation element guides 420, 422, 424 may be pre-compressed along substantially their entire lengths. According to another exemplary embodiment, the actuation element guides may be pre-compressed along a portion of their axial lengths. Turning to FIG. 26, an exemplary embodiment of a bundle 1800 of actuation element guides is schematically depicted. As shown in the exemplary embodiment of FIG. 26, bundle 1800 may include a first portion 1810 of straight actuation element guides and a second portion 1820 of twisted element guides (e.g., twisted about a longitudinal axis 1870 of bundle 1800). First portion 1810 may have a length corresponding to a portion of an instrument (that includes bundle 1800) not substantially bent when the instrument is inserted into a cannula having a curved section, while second portion 1820 may have a length corresponding to the curved section (e.g., curved section 322 of cannula 320 in FIG. 3) of the cannula so the pre-compressed actuation element guides of section portion 1820 may compensate for changes in length of actuation elements extend through the actuation element guides of bundle 1800 when the instrument is bent in the curved section of the cannula.

First portion 1810 may extend, for example, from a proximal end 1802 of bundle 1800 and join second portion 1820, which extends to a distal end 1804 of bundle 1800. According to an exemplary embodiment, proximal end 1802 may be disposed within a force transmission mechanism of an instrument and distal end 1804 may be disposed within a distal portion of an instrument. The actuation element guides of first portion 1810 and second portion 1820 may be connected to one another so that actuation elements extending through the straight actuation element guides of first portion 1810 extend through corresponding actuation element guides of second portion 1820. According to an exemplary embodiment, bundle 1800 may include a proximal block 1830 and a distal block 1840 to pre-compress actuation element guides of second portion 1820, such as according to the exemplary embodiments of FIGS. 9-17, except that bundle 1800 may include a fitting 1832 holding actuation element guides of first portion 1810 in a straight configuration but permitting actuation element guides of second portion 1820 to assume non-linear shapes in their pre-compressed state. According to an exemplary embodiment, proximal portion 1802 and/or distal portion 1804 of bundle 1800 may be fixed to an instrument including bundle 1800, so that when the shaft of the instrument including bundle 1800 is rolled in the directions indicated by arrows 1872 about axis 1870, both portions 1810, 1820 of bundle 1800 are also rolled. According to an exemplary embodiment, proximal block 1830 is fixed to an instrument, with portions 1810 and 1820 free to move relative to proximal block 1830. For example, portions 1810 and 1820 twist relative to proximal block 1830, such as when distal block 1840 is fixed to an instrument shaft (not shown) and rolls with the instrument shaft.

The exemplary embodiments and methods described herein have been described as being utilized with surgical instruments for teleoperated surgical systems. However, the exemplary embodiments and methods described herein may be used with other surgical devices, such as laparoscopic instruments and other hand held instruments. Further, the exemplary embodiments and methods may be employed in other applications that use remotely actuatable components. For instance, the exemplary embodiments described herein may be used in devices used for pipe inspection and other devices utilizing remote access via teleoperation or manual actuation.

By providing pre-compressed actuation element guides as described in the various exemplary embodiments herein, the actuation element guides may compensate for changes in length of actuation elements extending through the actuation element guides, such as when the actuation element guides extend through a curved section of a cannula. As a result, changes of length of the actuation elements is minimized or eliminated, which could otherwise interfere with the functioning of the actuation elements to actuate an instrument, such as, for example, to actuate an end effector and/or wrist of an instrument.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the claims being entitled to their full breadth and scope, including equivalents.

What is claimed is:

1. A surgical instrument, comprising:
   a shaft extending along a longitudinal axis, the shaft comprising a bendable portion;
   a force transmission mechanism disposed at a first end of the shaft;
   an end effector disposed at a second end of the shaft;
   an actuation element extending along the shaft and operably coupling the force transmission mechanism to the end effector, the actuation element being configured to transmit an actuation force from the force transmission mechanism to the end effector; and
   an actuation element guide extending along at least the bendable portion of the shaft, wherein the actuation element guide defines a lumen in which the actuation element is received;
   a first block at a first end of the actuation element guide; and
   a second block at a second end of the actuation element guide opposite the first end;
   wherein, in the absence of both a bending of the bendable portion of the shaft and the actuation force applied to the actuation element, the actuation element guide is under a longitudinal pre-compression force applied to the actuation element guide by the first block and the second block.

2. The surgical instrument of claim 1, wherein the shaft comprises an inner wall defining a hollow, open space within the shaft between the inner wall and the actuation element guide.

3. The surgical instrument of claim 1, wherein the actuation element guide is a tube.

4. The surgical instrument of claim 1, wherein:
   a longitudinal position of the first block or the second block is adjustable with reference to the shaft; and
   an amount of the longitudinal pre-compression force is set based on a relative position of the first and second blocks with reference to the shaft.

5. The surgical instrument of claim 4, further comprising set screws configured to set a longitudinal position of the first block or the second block with reference to the shaft.

6. The surgical instrument of claim 4, further comprising a fitting fixed to an interior surface of the shaft, wherein one of the first and second blocks is engaged with the fitting to set a position of the one of the first and second blocks that sets the longitudinal pre-compression force on the actuation element guide.

7. The surgical instrument of claim 6, wherein the fitting is fixed to the interior surface of the shaft via a weld.

8. The surgical instrument of claim 1, wherein the actuation element guide is laterally unconstrained within the shaft between the first block and the second block.

9. The surgical instrument of claim 1, wherein at least a portion of the actuation element guide has a non-linear shape in a straight configuration of the shaft.

10. The surgical instrument of claim 1, further comprising a wrist disposed between the shaft and the end effector.

11. An instrument, comprising:
a shaft comprising a first end and a second end opposite the first end;
a force transmission mechanism at the first end of the shaft;
a first actuation element guide extending from the first end of the shaft, through the shaft, and to the second end of the shaft;
a second actuation element guide extending from the first end of the shaft, through the shaft, and to the second end of the shaft;
a first actuation element operably coupled to the force transmission mechanism and extending from the first end of the shaft, through the first actuation element guide, to the second end of the shaft;
a second actuation element operably coupled to the force transmission mechanism and extending from the first end of the shaft, through the second actuation element guide, to the second end of the shaft;
a first block at the first end of the shaft; and
a second block at the second end the shaft;
wherein the first actuation element guide comprises a first end in contact with the first block and a second end in contact with the second block,
wherein the second actuation element guide comprises a first end in contact with the first block and a second end in contact with the second block; and
wherein, in the absence of both a bending of the shaft and an actuation force applied to the first actuation element, the second actuation element, or both the first and second actuation elements, the first actuation element guide and the second actuation element guide are under a longitudinal pre-compression force applied by the first block and the second block along at least a portion of an axial length of the shaft.

12. The instrument of claim 11, wherein the shaft comprises an inner wall defining a hollow, open space within the shaft between the inner wall and the first and second actuation element guides.

13. The instrument of claim 11, wherein:
the first and second ends of the shaft define a longitudinal axis of the shaft; and
the shaft is bendable relative to the longitudinal axis of the shaft.

14. The instrument of claim 11, wherein:
the instrument further comprises an end effector at the second end of the shaft; and
at least one of the first actuation element and second actuation element are operably coupled to the end effector to transmit an actuation force from the force transmission mechanism to actuate the end effector.

15. The instrument of claim 11, wherein:
the instrument further comprises a wrist at the second end of the shaft; and
at least one of the first actuation element and the second actuation element are operably coupled to the wrist to transmit an actuation force from the force transmission mechanism to actuate the wrist.

16. The instrument of claim 11, wherein an amount of the longitudinal pre-compression force is set based on a position of the first and second blocks with reference to the shaft.

17. The instrument of claim 11, wherein one or both of the first actuation element guide and the second actuation element guide are laterally unconstrained within the shaft between the first block and the second block.

18. The instrument of claim 11, wherein:
a central longitudinal axis of the shaft is defined between the first and second ends of the shaft; and
one or both of the first actuation element guide and the second actuation element guide are offset from a central longitudinal axis of the shaft.

* * * * *